(12) United States Patent
Zenz-Olson et al.

(10) Patent No.: US 12,226,307 B2
(45) Date of Patent: Feb. 18, 2025

(54) INDIVIDUALLY LOCKABLE CINCH LOOP MICRO SUTURE ANCHOR ARRAY FOR HIGH DENSITY ANATOMICAL ATTACHMENT OF SOFT TISSUE TO BONE

(71) Applicant: Integrity Orthopaedics, Inc., Orono, MN (US)

(72) Inventors: Zak Zenz-Olson, Ham Lake, MN (US); Nathaniel Van Tran, Lakeville, MN (US); Thomas A. Westling, Orono, MN (US); Patrick M. Connor, Charlotte, NC (US); Howard W. Harris, Southlake, TX (US); Marc Labbé, Spring, TX (US); David M. Crompton, St. Paul, MN (US)

(73) Assignee: Integrity Orthopaedics, Inc., Maple Plain, MN (US)

( * ) Notice: Subject to any disclaimer, the term of this patent is extended or adjusted under 35 U.S.C. 154(b) by 504 days.

(21) Appl. No.: 17/680,003

(22) Filed: Feb. 24, 2022

(65) Prior Publication Data

US 2022/0323199 A1 Oct. 13, 2022

Related U.S. Application Data

(60) Provisional application No. 63/281,411, filed on Nov. 19, 2021, provisional application No. 63/249,875, (Continued)

(51) Int. Cl.
*A61F 2/08* (2006.01)
*A61B 17/04* (2006.01)

(52) U.S. Cl.
CPC ........ *A61F 2/0811* (2013.01); *A61B 17/0401* (2013.01); *A61B 2017/0404* (2013.01);
(Continued)

(58) Field of Classification Search
CPC ............ A61F 2/0811; A61F 2002/0829; A61F 2002/0852; A61F 2002/0882;
(Continued)

(56) References Cited

U.S. PATENT DOCUMENTS

| 4,899,743 A | 2/1990 | Nicholson et al. |
| 4,968,315 A | 11/1990 | Gatturna |

(Continued)

*Primary Examiner* — Katherine H Schwiker
*Assistant Examiner* — Lauren Dubose
(74) *Attorney, Agent, or Firm* — Seager, Tufte & Wickhem LLP

(57) ABSTRACT

A system of toggle type suture anchors is disclosed. The plurality of suture anchors is connected in series by a plurality of independently cinchable working suture loops with one working suture loop connecting each pair of anchors in series to form a chain. Each of the suture anchors as connected by working suture loops allows tensioning of the working suture between itself and the prior anchor implanted in the serial string. Further, each anchor includes a loop type locking mechanism to lock the cinchable working suture loop subsequent to tensioning so that the loop remains fixed in size during cyclic loading during joint use. This creates an independently tensioned suture stitch between each implanted suture anchor and the just previously implanted anchor. In total the system as implanted creates a high density, continuous array of anchor-to-anchor stitches for robust securement of soft tissue to bone.

20 Claims, 14 Drawing Sheets

Related U.S. Application Data filed on Sep. 29, 2021, provisional application No. 63/172,613, filed on Apr. 8, 2021.

(52) U.S. Cl.
CPC .............. A61B 2017/0414 (2013.01); A61B 2017/0458 (2013.01); A61B 2017/0464 (2013.01); A61B 2017/0496 (2013.01); A61F 2002/0829 (2013.01); A61F 2002/0852 (2013.01)

(58) Field of Classification Search
CPC ........ A61B 17/0401; A61B 2017/0404; A61B 2017/0414; A61B 2017/0458; A61B 2017/0464; A61B 2017/0496; A61B 2017/0475; A61B 2017/0409; A61B 2017/0459

See application file for complete search history.

(56) References Cited

U.S. PATENT DOCUMENTS

| | | |
|---|---|---|
| 5,041,129 A | 8/1991 | Hayhurst et al. |
| 5,192,303 A | 3/1993 | Gatturna et al. |
| 5,203,787 A | 4/1993 | Noblitt et al. |
| 5,207,679 A | 5/1993 | Li |
| 5,269,809 A | 12/1993 | Hayhurst et al. |
| 5,403,348 A | 4/1995 | Bonutti |
| 5,405,359 A | 4/1995 | Pierce |
| 5,468,197 A | 11/1995 | Loeffler |
| 5,584,835 A | 12/1996 | Greenfield |
| 5,626,614 A | 5/1997 | Hart |
| 5,669,935 A | 9/1997 | Rosenman et al. |
| 5,683,418 A | 11/1997 | Luscombe et al. |
| 5,725,557 A | 3/1998 | Gatturna et al. |
| 5,728,100 A | 3/1998 | Skiba |
| 5,741,300 A | 4/1998 | Li |
| 5,810,848 A | 9/1998 | Hayhurst |
| 5,891,168 A | 4/1999 | Thal |
| 5,921,986 A | 7/1999 | Bonutti |
| 5,948,002 A | 9/1999 | Bonutti |
| 5,961,538 A | 10/1999 | Pedlick et al. |
| 6,056,773 A | 5/2000 | Bonutti |
| 6,066,160 A | 5/2000 | Colvin et al. |
| 6,117,161 A | 9/2000 | Li et al. |
| 6,270,518 B1 | 8/2001 | Pedlick et al. |
| 6,293,961 B2 | 9/2001 | Schwartz et al. |
| 6,451,030 B2 | 9/2002 | Li et al. |
| 6,500,195 B2 | 12/2002 | Bonutti |
| 6,520,980 B1 | 2/2003 | Foerster |
| 6,527,795 B1 | 3/2003 | Lizardi |
| 6,547,800 B2 | 4/2003 | Foerster et al. |
| 6,592,609 B1 | 7/2003 | Bonutti |
| 6,645,227 B2 | 11/2003 | Fallin et al. |
| 6,660,023 B2 | 12/2003 | McDevitt et al. |
| 6,726,707 B2 | 4/2004 | Pedlick et al. |
| 6,773,436 B2 | 8/2004 | Donnelly et al. |
| 6,843,799 B2 | 1/2005 | Bartlett |
| 6,972,027 B2 | 12/2005 | Fallin et al. |
| 6,986,781 B2 | 1/2006 | Smith |
| 7,041,120 B2 | 5/2006 | Li et al. |
| 7,081,126 B2 | 7/2006 | McDevitt et al. |
| 7,232,455 B2 | 6/2007 | Pedlick et al. |
| 7,320,701 B2 | 1/2008 | Haut et al. |
| 7,556,640 B2 | 7/2009 | Foerster |
| 7,566,339 B2 | 7/2009 | Fallin et al. |
| 7,641,672 B2 | 1/2010 | Fallin et al. |
| 7,645,293 B2 | 1/2010 | Martinek et al. |
| 7,658,751 B2 | 2/2010 | Stone et al. |
| 7,674,275 B2 | 3/2010 | Martin et al. |
| 7,682,374 B2 | 3/2010 | Foerster et al. |
| 7,722,644 B2 | 5/2010 | Fallin et al. |
| 7,803,173 B2 | 9/2010 | Burkhart et al. |
| 7,806,909 B2 | 10/2010 | Fallin et al. |
| 7,875,064 B2 | 1/2011 | Donnelly et al. |
| 7,909,851 B2 | 3/2011 | Stone et al. |
| 7,963,972 B2 | 6/2011 | Foerster et al. |
| 8,052,719 B2 | 11/2011 | Paulos |
| 8,118,835 B2 | 2/2012 | Weisel et al. |
| 8,298,262 B2 | 10/2012 | Stone et al. |
| 8,348,975 B2 | 1/2013 | Dreyfuss |
| 8,366,744 B2 | 2/2013 | Bojarski et al. |
| 8,419,794 B2 | 4/2013 | ElAttrache et al. |
| 8,425,536 B2 | 4/2013 | Foerster et al. |
| 8,449,584 B2 | 5/2013 | Donnelly et al. |
| 8,454,655 B2 | 6/2013 | Yeung et al. |
| 8,512,375 B2 | 8/2013 | Torrie et al. |
| 8,771,314 B2 | 7/2014 | Crombie et al. |
| 8,777,992 B2 | 7/2014 | Yeung et al. |
| 8,814,905 B2 | 8/2014 | Sengun et al. |
| 8,821,503 B2 | 9/2014 | Tornier et al. |
| 8,828,052 B2 | 9/2014 | Caborn et al. |
| 8,845,699 B2 | 9/2014 | Bonutti |
| 8,932,331 B2 | 1/2015 | Kaiser et al. |
| 8,951,287 B1 | 2/2015 | Green et al. |
| 8,986,346 B2 | 3/2015 | Dreyfuss |
| 9,072,509 B2 | 7/2015 | Stoll, Jr. et al. |
| 9,173,651 B2 | 11/2015 | Stone et al. |
| 9,192,369 B2 | 11/2015 | Bittenson |
| 9,216,036 B2 | 12/2015 | Johnstone |
| 9,220,493 B2 | 12/2015 | Hart et al. |
| 9,265,495 B2 | 2/2016 | Petersen et al. |
| 9,271,714 B2 | 3/2016 | Martin |
| 9,301,756 B2 | 4/2016 | Wardle |
| 9,307,979 B1 | 4/2016 | Bennett et al. |
| 9,314,238 B2 | 4/2016 | Martin |
| 9,345,467 B2 | 5/2016 | Lunn et al. |
| 9,345,468 B2 | 5/2016 | Sengun et al. |
| 9,421,012 B2 | 8/2016 | Orphanos et al. |
| 9,451,945 B2 | 9/2016 | Hawkins |
| 9,463,008 B2 | 10/2016 | Thal |
| 9,463,013 B2 | 10/2016 | Pilgeram et al. |
| 9,468,433 B2 | 10/2016 | Denham et al. |
| 9,486,211 B2 | 11/2016 | Stone et al. |
| 9,504,462 B2 | 11/2016 | Dooney, Jr. et al. |
| 9,526,489 B2 | 12/2016 | Burkhart |
| 9,532,777 B2 | 1/2017 | Kaiser et al. |
| 9,532,778 B2 | 1/2017 | Sengun et al. |
| 9,539,000 B2 | 1/2017 | Hendricksen et al. |
| 9,539,003 B2 | 1/2017 | Stone et al. |
| 9,545,251 B2 | 1/2017 | Bojarski et al. |
| 9,597,070 B2 | 3/2017 | Bittenson |
| 9,655,611 B2 | 5/2017 | Green et al. |
| 9,693,765 B2 | 7/2017 | Sullivan et al. |
| 9,713,463 B2 | 7/2017 | Oren et al. |
| 9,763,719 B2 | 9/2017 | Snyder et al. |
| 9,795,373 B2 | 10/2017 | Sengun |
| 9,801,620 B2 | 10/2017 | Kaiser et al. |
| 9,814,565 B2 | 11/2017 | Foerster et al. |
| 9,833,229 B2 | 12/2017 | Hernandez et al. |
| 9,861,351 B2 | 1/2018 | Kaiser et al. |
| 9,872,678 B2 | 1/2018 | Spenciner et al. |
| 9,895,145 B2 | 2/2018 | Sengun et al. |
| 9,931,150 B2 | 4/2018 | Philippon et al. |
| 9,962,150 B2 | 5/2018 | Rodriguez et al. |
| 9,993,241 B2 | 6/2018 | Denham et al. |
| 10,130,354 B2 | 11/2018 | Dooney, Jr. |
| 10,172,607 B2 | 1/2019 | Burkhart |
| 10,178,989 B2 | 1/2019 | Bennett et al. |
| 10,188,378 B2 | 1/2019 | Lunn et al. |
| 10,285,684 B2 | 5/2019 | Spenciner et al. |
| 10,368,856 B2 | 8/2019 | Stone et al. |
| 10,376,260 B2 | 8/2019 | Bojarski et al. |
| 10,398,428 B2 | 9/2019 | Denham et al. |
| 10,478,172 B1 | 11/2019 | Williams et al. |
| 10,492,774 B2 | 12/2019 | Larsen |
| 10,543,075 B2 | 1/2020 | Gregoire et al. |
| 10,575,842 B2 | 3/2020 | Lund |
| 10,582,919 B2 | 3/2020 | Hirotsuka et al. |
| 10,588,614 B2 | 3/2020 | Gittings et al. |
| 10,595,845 B2 | 3/2020 | Burkhart et al. |
| 10,603,028 B2 | 3/2020 | Sengun et al. |
| 10,603,029 B2 | 3/2020 | Kaiser et al. |

(56) References Cited

U.S. PATENT DOCUMENTS

| | | |
|---|---|---|
| 10,667,803 B2 | 6/2020 | Lizardi |
| 10,675,015 B2 | 6/2020 | Guo et al. |
| 10,695,047 B2 | 6/2020 | Sengun |
| 10,729,421 B2 | 8/2020 | Stone et al. |
| 10,772,622 B2 | 9/2020 | Santangelo et al. |
| 10,786,235 B2 | 9/2020 | Sorensen et al. |
| 10,863,979 B2 | 12/2020 | Sorensen et al. |
| 10,881,500 B2 | 1/2021 | Brunsvold et al. |
| 10,898,179 B2 | 1/2021 | Dreyfuss et al. |
| 10,912,549 B2 | 2/2021 | Sengun et al. |
| 10,952,719 B2 | 3/2021 | Lombardo et al. |
| 10,966,704 B2 | 4/2021 | Lozier et al. |
| 10,987,099 B2 | 4/2021 | Stone et al. |
| 2002/0019649 A1* | 2/2002 | Sikora ............... A61B 17/0401 606/232 |
| 2005/0187577 A1* | 8/2005 | Selvitelli ............ A61B 17/0401 606/232 |
| 2006/0178702 A1 | 8/2006 | Pierce et al. |
| 2009/0312782 A1 | 12/2009 | Park |
| 2011/0022061 A1* | 1/2011 | Orphanos .......... A61B 17/0469 606/232 |
| 2013/0190815 A1 | 7/2013 | Mansmann |
| 2015/0250470 A1 | 9/2015 | Vargas |
| 2019/0290256 A1 | 9/2019 | Kehoe |
| 2020/0155299 A1 | 5/2020 | Lund |
| 2020/0253715 A1 | 8/2020 | Trenhaile |
| 2020/0315775 A1 | 10/2020 | Pilgeram et al. |
| 2021/0100547 A1 | 4/2021 | Schmieding |
| 2021/0228203 A1 | 7/2021 | Denham et al. |

\* cited by examiner

INDIVIDUALLY LOCKABLE CINCH LOOP MICRO SUTURE ANCHOR ARRAY FOR HIGH DENSITY ANATOMICAL ATTACHMENT OF SOFT TISSUE TO BONE

CROSS REFERENCE TO RELATED APPLICATIONS

The present application claims the benefit of and priority to U.S. Prov. Pat. App. No. 63/249,875, filed Sep. 29, 2021, and titled INDIVIDUALLY LOCKABLE CINCH LOOP MICRO SUTURE ANCHOR ARRAY FOR HIGH DENSITY ANATOMICAL ATTACHMENT OF SOFT TISSUE TO BONE, U.S. Prov. Pat. App. No. 63/172,613, filed Apr. 8, 2021, and titled KNOTLESS MICRO SUTURE ANCHOR ARRAY FOR HIGH DENSITY ANATOMICAL ATTACHMENT OF SOFT TISSUE TO BONE, and U.S. Prov. Pat. App. No. 63/281,411, filed Nov. 19, 2021, titled DELIVERY DEVICE FOR IMPLANTING KNOTLESS MICRO-SUTURE ANCHORS AND ANCHOR ARRAYS FOR ATTACHMENT OF SOFT TISSUE TO BONE, the disclosures of which are incorporated herein by reference.

BACKGROUND

Throughout the human body there are many attachments of soft tissue, such as tendons and ligaments, to bone as integral elements of motion in functioning joints such as the shoulder. The shoulder joint includes the humeral head of the upper arm bone in contact with the indentation of the glenoid working in conjunction with the rotator cuff, which is a combination of muscles and tendons forming a capsule that both stabilizes the joint and causes desired motion. Injury to the connection between tendons of the rotator cuff muscles to the humeral head, usually a tear in a tendon, is common. These tears do not self-heal. It is estimated that in the U.S. over 4 million people annually are referred to a surgeon due to shoulder pain and over 500,000 of these referrals result in shoulder surgery to repair the rotator cuff.

Significant effort has been expended over the past 30 years to develop bone and tissue anchor devices and methods to respond to the need for effective rotator cuff repair. Early methods and devices utilized an open surgical technique that required a large incision of 4 to 6 cm and cutting the deltoid muscle, then re-attaching after the rotator cuff repair. This method is still used today for massive tears by some surgeons due to high success rate, however, the procedure is associated with deltoid dysfunction, significant pain during recovery and extensive rehabilitation time. Due to the invasiveness of the open surgery and resulting rehabilitation time, a "mini-open" procedure and associated devices were developed in the early 1990's, wherein the surgeon uses a partial arthroscopic technique followed by an incision and split of the deltoid muscle fibers to access the rotator cuff tendon for repair. By the late 1990's, devices and instruments were further developed to complete the repair of rotator cuff tendon attachment to bone using all-arthroscopic techniques, with further resultant reduction in trauma and recovery time.

Arthroscopic repair of the rotator cuff tendon attachments to the humeral head is the most common technique used today. However, it is recognized that these all-arthroscopic techniques are quite difficult to perform and achieve varying results. The skill of the surgeon with the technology available is a known factor related to the procedure's success. Even with the last 20 years of all-arthroscopic technologic advancement and experience, deficiencies persist as evidenced by studies indicating an overall average rotator cuff repair failure rate of 20% to 40%, with a highly variable range of 4% to 90% in individual studies. The study results indicate failure rates are much higher for large or massive tendon tears and there are vast variations in failure rates between surgeons, as well as with respect to various patient factors, equipment used, and type of repair completed.

There is significant controversy among professionals as to the reasons for the high incidence of arthroscopic rotator cuff repair failure (i.e., "re-tear of the rotator cuff"). However, studies clearly show there is a need to reduce the failure rate of arthroscopic rotator cuff repair to avoid its effects of patients' lack of mobility, functional deficits, increased pain and/or requiring subsequent and more invasive surgery with the attendant pain and rehabilitation. In particular, there is great concern for patients who have some degree of native tendon or repair tendon failure yet choose to "live with it" rather than going through a first or another surgery and rehabilitation, thus affecting quality of life and promoting continued joint degradation from lack of use.

The basic device or devices used for repair of a tendon torn from a bone is one or more suture anchors in which a mechanical structure provides an anchor to the bone and a suture or sutures extend therefrom for attachment to the soft tissue or tendon. Many types of anchor technologies have been proposed and used in procedures. A review of the prior art patent literature indicates over a thousand designs for suture anchors, bone anchors, tendon repair systems, delivery devices and methods espousing improved features over the past 25 years, yet repair failure rate is still unacceptable indicating the need for further improvement in the area of arthroscopic reattachment of tendons to bone and in particular in rotator cuff repair.

OVERVIEW

The present inventors have recognized, among other things, that a problem to be solved is the need for new and/or alternative devices and methods for arthroscopically affixing a tendon or other soft tissue to bone such as in rotator cuff repair with low failure rate, preferably under 10% on average, with little variation between surgeons, patient characteristics, and the system/method used for repair. The disclosed devices, systems, and methods, along with a statement of the problem being solved by each element are included in summary form followed by a description of specific claimed structure or methods in the present disclosure. Importantly, the invention is directed to a system and method wherein the implanted array of anchors, with a continuous set of anchor-to-anchor suture stitches, creates a seam-like attachment akin to a sewing machine construct.

The present disclosure includes a total system for re-attaching a tendon that has at least in part torn away from a bone attachment or footprint. The system is useful in repair of a rotator cuff tendon that has torn away from a bone, but may also be used in other procedures elsewhere in the body. The system is particularly useful in repair of the rotator cuff by reattaching a torn tendon, such as the most-commonly-torn supraspinatus tendon, to the humeral head of the arm. In larger tears, the infraspinatus tendon may also be torn and amenable to repair with this system. The repair is an anatomical repair, meaning that the system, devices and methods result in a repaired tendon and bone combination that closely approximates the prior natural, anatomic relationship between that tendon and bone to promote healing and provide pain free full function to the healed repair. An anatomical repair using the presently described system may also seal the tendon in position, taking advantage of local synovial fluid to aid healing and improve post-surgery function. The system may also be used to reinforce partial tears and to secure areas beyond the region of a full-thickness tear as needed. Further, the system, as implanted can dramatically reduce recovery and rehabilitation time due to the robust nature of the repair immediately following surgery, requiring less time using a sling to limit mobility and allowing early physical therapy to maintain pre-surgery mobility and strength during healing. It is believed time in a sling and complete recovery time can be reduced at least 50%, while reducing the average failure rate to less than 10% with the current disclosed system.

As stated, in preferred examples, the exemplary rotator cuff repair is an anatomical repair in that the repaired tendon nearly duplicates or closely approximates the natural tendon and bone relationship in the fully functional joint. In illustrative examples, the tendon/tendons is/are substantially and completely re-attached to the original footprint on the bone from which it was torn. The original footprint area provides the greatest likelihood of healing re-attachment of the tendon to the bone while restoring anatomy. By substantially re-attached to the original footprint it is meant that a substantial portion of the remaining torn tendon surface that was originally attached to the footprint is re-attached thereto. The current system makes possible close approximation of the original tendon attachment by allowing transtendinous, or through the tendon, implantation of each anchor. Thus, the tendon is held in the desired location when the anchor is installed, unlike current systems that insert anchors into exposed bone through a tear and then use suture passers (which pass the suture when the tendon is not in position) to approximate where the surgeon believes the tendon will pull down to the footprint. Further, the anatomical repair reduces micromotion at the bone to tendon interface so that healing is promoted, even during movement of the joint. Finally, access to blood for healing is improved due to utilizing substantially more small holes in the proximal humerus to accommodate a large number of anchors in a close array.

In fresh cadaveric studies, using the presently disclosed system, the repaired tendon and bone combination provide a tensile strength upon re-attachment of greater than 400 Newtons (N) and initial cyclic creep or gap formation of less than 2 millimeters (mm) when cycled to a peak load on the repaired tendon per cycle of 180 N. Initial cyclic creep measures the rigidity or robustness of the attachment of the tendon to the bone as it measures how much the tendon slides or moves relative to the bone attachment. Low initial cyclic creep allows the potential for faster healing and less need for sling immobilization. Creep of less than 2 mm., or even less than 1 mm. is therefore a preferred outcome in some examples. In other words, if the tendon stays fixed in position relative to the bone it is compressed against (i.e., reduced micromotion), the healing process will occur more quickly and predictably than a situation that includes sliding of the tendon back and forth relative to the bone.

In preferred examples, the anatomic repair requires a high-density array of knotless small anchors (requiring a bone hole size for insertion of less than 3 mm) with close spacing between anchors (less than 7 mm edge to edge, or less than 10 mm hole center to hole center) to create anchor to subsequent anchor suture stitches that apply many points of constant independent force on the tendon against the bone. By independent it is meant that failure of one suture stitch to apply adequate force, as would happen if the suture stitch broke, does not affect other suture stitches. Naturally, the number of anchors utilized in a repair will depend upon the size of the tear.

It is recognized in the art that rotator cuff tears are classified into four categories based on tear size and whether a single row or double row repair is completed. Small tears are less than 1 centimeter (cm) in length; medium tears are 1 cm to 3 cm in length; large tears are 3 cm to 5 cm in length and massive tears are greater than 5 cm in length. With current devices, surgeons are limited to available large anchors and by the size of the tear as the medial anchors must fit in the tear area. For example, surgeons may use about 1 medial anchor on small tears, 1 or 2 medial anchors on medium tears and 2 or 3 medial anchors on large tears and massive tears. With the high anchor density anatomical repair of the present application, the surgeon is not limited by tear size as the anchors are implanted through the tendon and can use greater than 3 medial anchors on small tears, greater than 5 medial anchors on medium tears, and greater than 6 medial anchors on large tears and massive tears. This may include positioning implants outside the area of a full thickness tear to reinforce areas of partial thickness tears or weaker untorn tendon. Further, the present suture anchors are designed for knotless tensioning and locking to expedite implantation, maximize reproducibility amongst surgeons, and not interfere with shoulder mobility from protruding knots while eliminating the tension variations that have been found in knotted suture anchors due to the difficulty of tying knots arthroscopically.

The suture anchors of the present disclosure are bar or toggle type anchors wherein the basic structure for bone attachment is a thin elongate and/or cylindrical body having a cross sectional diameter of less than about 3 mm and a length of about 6 mm to about 10 mm. Although described as generally cylindrical, it is recognized that certain surfaces can be machined or molded flat or grooved to allow for suture strands to run alongside the implant when placed in a circular delivery tube. That is, rather than cylindrical, the present anchors may be polygonal, for example, hexagonal or octagonal, or other cross-sectional shape.

The anchor may be a through the tendon or transtendinous implant as described with respect to the delivery device and method below. Being transtendinous eliminates the requirement of placing the anchors only where the tendon is absent from the bone such as in the hole formed by the tear or outside the tendon footprint. Furthermore and importantly, the need for suture passing through the tendon is eliminated. Transtendinous implantation with many anchors used today includes technical challenges, including working a 3 mm to 6 mm diameter anchor through a hole in the tendon with an awl, damaging the tendon when passed through. Further, threaded and flanged type anchor retention features may also damage the tendon during passing.

With a toggle-type anchor, the anchor is inserted through a hole in the bone just larger than the anchor axial outer diameter. Within the bone, the anchor is toggled (aka flipped or rotated) about 90 degrees so that force applied to sutures extending from the toggle body pulls the length of the toggle body against the inner surface of the cortical shell of the humeral head. The degree to which the toggle body rotates or moves toward the cortical shell is affected by the quality of the bone and by individual patient traits, such as age, sex, location of the hole in the bone and degree of bone degradation due to the tear. The toggle body of the current invention is designed to toggle and seat with adequate pullout strength over the range of bone qualities encountered.

In some embodiments the toggle body includes one or more holes passing through the toggle body generally perpendicular to the longitudinal axis (preferably a minimum of three and maximum of 5 holes in some embodiments). The holes provide attachment for working suture loops that extend between successive anchors to connect the anchors in a serial chain with each suture loop designed to be collapsed or tensioned upon implantation of the two successive anchors which a particular loop connects. This forms the tensioned stitch between anchors that hold the tendon firmly against bone. Further, one hole on the anchor or the anchor body itself can carry a locking suture for locking each individual working suture loop when tensioned so that under cyclic loading during use the suture loop does not loosen or lengthen. The suture lock is a collapsible loop surrounding a portion of the working suture loop proximate the knot or structure that allows the working suture loop to change size or collapse when tensioned. The suture lock tightens around the working suture and locks it in position relative to the toggle body.

In some embodiments, the tightening of the suture lock pulls a small portion of the working suture of the working suture loop into a slot or channel in the bottom of the anchor. The working suture is pinched in a tortuous path that provides a sound lock and prevents sliding of the working suture relative to the anchor once the suture is appropriately tensioned. The strength of the lock is enhanced by the overall tortuous path followed by the working suture when the anchor is pulled against the cortical shell as the working suture goes through several near 90-degree turns which provide increased friction against the toggle body as well as the friction applied by the suture lock.

Each individual anchor includes features that assure it will implant properly through the tendon in a hole punched through the cortical shell of the humeral head. The anchor is inserted lengthwise through this hole into the spongy or cancellous bone. It is pushed by the point of a bone punch that mates with a dimple formed in the proximal end of the implant. The mating surface dimple is shaped to help maintain contact between the anchor and the punch while also allowing the anchor to pivot, rotate, or toggle from an insertion configuration in which the central axis of the anchor is aligned with the central axis of the punch to an implant configuration in which the central axis of the anchor no longer aligns with the central axis of the punch. The rotation or toggling may have two parts: an initial change of axial direction as the anchor passes beyond the cortical shell into the cancellous bone during advancement as the punch is used to push the anchor, and a second change of axial direction under tension applied using the working suture loop limbs as described below. The cancellous bone varies greatly in properties by location and patient ranging from very soft and porous to hard cellular structures depending upon many patient-specific factors. The included features of the present anchor assure proper toggled retention within the bone over the range of cortical shell and cancellous bone variations.

First, the implantable anchor preferably includes an acute angle on the distal surface with the upper side projecting further longitudinally than the lower side. Inserted this way, the longer portion engages the cancellous bone and begins rotation during anchor insertion. With both limbs of potentially one or two working suture loops extending up through the bone hole, one can pull the more distal working suture loop selectively, which further rotates the anchor body. In some examples the rotation may be to an angle of about 90 degrees relative to the central axis of the bone hole, though this extent of rotation is not necessary to the inventive concept. It has been found with other designs that in hard cancellous bone, the pulling on the distal suture at times may not cause rotation because the proximal portion is held rigid by a hard layer of cancellous bone and therefore pulling causes the anchor body to back out of the hole and lie under the tendon. To prevent this, the anchor body includes a fin or fins on the proximal portion that upon delivery project proximally and radially with a cross dimension greater than that of the bone hole. The size of the fins prevents back out of the anchor but also the fins are located to project and to catch on the cancellous bone and assist in rotation.

In a preferred embodiment, the present disclosure is directed to a plurality of anchors that are pre-strung to form a serial chain of anchors with an independent cinchable working suture loop connecting each anchor to a subsequent anchor in the chain. The anchor chain defines a set that forms an implanted array having a tensioned suture stitches extending from one anchor to the subsequent anchor in the pre-strung chain. Each tensioned suture stitch is formed when a working suture loop connecting two anchors as implanted is tensioned. Once tensioned, each working suture loop is equipped with a suture lock proximate an anchor. A chain of anchors can carry in the range of about 8 to 12 anchors in some preferred embodiments.

The high-density array of anchors is formed by implantation of the anchors in a chain or row which can be a relatively straight line or curve depending upon the tear to be repaired. A delivery device designed for sequential transtendinous implantation of each anchor in the array includes an elongated tube with a lumen therethrough having an anchor delivery tube therein with a short nub and a bone punch extending from a distal end of the elongate tube and anchor delivery tube. The bone punch extends beyond the short nub in an extended position. In use, the distal end of the three-part assembly (bone punch, nub and elongate tube) which leads with the distal tip of the punch, is positioned at a selected location on top of the tendon as properly positioned on the bone beneath. The assembly is tapped so that the punch penetrates the tendon and the bone while the nub follows and extends into the bone hole at least a short distance. The assembly is inserted until the distal end of the elongate tube is in desired contact with the tendon surface. At this point the punch is withdrawn proximally while the nub maintains registration with the formed hole in bone and the elongate tube is pressed against the tendon surface. A first anchor is loaded into the elongate tube proximal portion and the punch is again moved distally to force the anchor/implant down the tube through the tendon along the nub and into the bone. The nub functions like a shoehorn to track the anchor through the spongy tissue of the tendon that has closed around the nub.

Once the first anchor is inserted to the full depth determined by the bone punch, the bone punch is withdrawn or removed. This action can also release the nub so that it can move proximally into the tube if needed as the implanted anchor is rotated and moved up against the inner cortical shell. In some examples, the nub is not merely released, but is actively retracted by the use of a linkage associated with an actuator in the anchor delivery tool handle that is configured to apply a positive force to the nub to retract. For example, once the anchor is implanted and the bone punch is removed, the nub may be fully retracted into the outer tube of the anchor delivery tool to prevent the nub damaging the working suture or suture lock during subsequent steps.

With the bone punch retracted, the suture loop limb or limbs is/are pulled to further rotate the anchor body and move it toward the cortical shell. When the first anchor is set in sufficiently strong material inside the bone (either within dense cancellous bone or resting against the undersurface of the cortical shell), and with the working suture locked relative to the first anchor, the delivery device can be moved for implantation of the next anchor. With the second and subsequent anchors, both a proximal and a distal suture portions of the working suture extend up through the delivery device. It is preferable that the distal portion of the working suture be pulled to cause rotation of the anchor while also allowing the working suture loop to close as the suture loop limb slides through the knot thereon. The slack extending to the previous anchor is therefore shortened. This is continued until the properly tensioned suture stitch is formed at which point the suture lock on the second or subsequent anchor is activated to maintain tension in the individual suture stitch by maintaining the working suture loop at the size as tensioned even under cyclic loading during use. The locking suture has a proximal extension that can be cut off after tightening in some examples. In other examples, the locking suture is a selectively breakable suture which can be used and such breakable portion is positioned proximate the slidable knot. For example, a second knot may be provided on the locking suture proximal of the slidable knot, or a nick may be created in the locking suture proximal of the slidable knot. The distal end of the anchor delivery tool may be pressed against the tendon during the rotating/toggling steps, during tensioning of the working suture, and while the suture lock is secured to provide a counterforce against back-out of the anchor and/or possible stress on or fracture of the cortical shell.

This is repeated for a desired number of anchors in the pre-strung chain which as implanted form a high-density array as described above. As can be understood, the number of suture stitches formed is equal to the number of anchors in the chain implanted minus 1. Further, the number of working suture loops equals the number of stitches as each loop forms a single stitch. Further, the string of stitches is continuous with each stitch tensioned and locked independently to form a required robust tendon attachment. The continuous string of stitches can form a row or chain of stitches of desired shape such as a linear row, a zig-zag shape, an arc, etc. as per surgeon discretion. By row or chain, it is meant that the suture stitches extend from one anchor to the next in the sequence of implanted anchors.

As previously stated, the distance between ends of a suture stitch (the distance between anchors) is preferably less than about 7 mm (if measuring from hole edge to hole edge; the distance may be 10 mm if measured hole center to hole center) to provide consistent force on the tendon against the bone to reduce creep. One particularly robust array of implanted anchors includes a first array implanted in a medial portion of the original tendon footprint to form a row or line of stitches generally perpendicular to the length or direction of the tendon's forces. A second array can then be implanted laterally nearer the edge of the tear with at least one anchor through the tendon while at least one other anchor is implanted laterally of the tendon edge to reapproximate the tendon properly against the bone. The lateral row can be implanted in a zig zag pattern or other appropriate pattern based on the shape of the tear. Depending upon tear size and location, multiple patterns can be utilized.

The present application is specifically directed to features of an implant system that utilize a pre-strung serially connected group of suture anchors that are linked so they can be tensioned from one anchor to a successive anchor and locked to form an independent tensioned suture stitch that holds the tendon anatomically in position. The specific features below should be studied in conjunction with the overall system to adequately assess each improvement.

In some preferred embodiments of the present invention, a pre-strung serially connected system of suture anchors is utilized to form an implanted array with serial anchor to anchor tensioned and independently locked suture stitches. In one preferred method for creating an implanted serial array of tensioned and independently locked anchor to anchor suture stitches to attach soft tissue to bone the array to be implanted is first provided. The array includes a pre-strung plurality of anchors. The first anchor has at least one passage therethrough and has a cinchable or collapsible suture loop extending therethrough. The cinchable working suture loop extends to a second anchor and passes through at least one hole in that anchor. The second anchor preferably has a second hole therethrough which has a second cinchable suture loop passing therethrough that extends to a third anchor having at least one hole therethrough. This is repeated for the length of the chain that can include 8 to 12 anchors in some embodiments. A plurality of anchors each connected serially by an independent cinchable working suture loop to a subsequent anchor is created. With implantation of any two serial anchors, the cinchable loop can be drawn tight or tensioned to form a suture stitch that overlays and compresses the tendon between the anchors and hold it tightly against the humeral head. Each of the anchor pair's cinchable loop further includes a separate locking loop, wherein the separate locking loop encircles a portion of the length of the suture of the cinchable loop or working suture loop adjacent the anchor. Each locking loop can have a first position allowing the suture to slide through the locking loop and a second position engaging the suture and preventing sliding within the locking loop due to its location relative to the toggle body hole or sliding knot of the cinchable loop. It is recognized that during surgery, simply tensioning the cinchable working suture loop will hold the tendon in proper repaired position against the bone, however, with such joints as the rotator cuff, the cinch loop would likely loosen during use of the joint after surgery, therefore the locking loop provides a positive lock on the cinch loop so that it remains tensioned as implanted.

In a preferred method, once the above serial array is in hand, a first anchor of the pre-strung plurality of anchors is implanted in bone. A second anchor in the pre-strung plurality of anchors is then implanted in bone spaced a selected distance from the first anchor. Tension is then applied to the cinchable loop via a tail extending from a slip knot adjacent the second anchor (or first anchor in alternative embodiments). The loop shrinks, slack between anchors is taken up and a tensioned stitch formed which presses the tendon against bone. Once tensioned, the cinchable suture loop is locked via the locking loop that is adjacent the slip knot and extends around the suture of the cinchable loop. When tightened around the working suture of the suture loop adjacent the slip knot, the cinchable loop is prevented from loosening as the tail cannot move within the slip knot. The tail of the cinchable loop can then be cut near the tendon surface while the locking loop tail preferably breaks at a positioned knot.

In some preferred embodiments the method is repeated for more anchors. For example, next a third anchor in the pre-strung plurality of anchors is implanted in bone spaced a selected distance from the second anchor. Tension is applied to the cinchable working suture loop extending from the second anchor and passing through the third anchor. Once tensioned to form a stitch holding the tendon to the bones as desired, the suture is then locked in the third anchor after tensioning to create a tensioned and locked stitch between the second and third anchor. These steps can be repeated for successive anchors in the pre-strung array. In other words, repeating the implanting, tensioning and locking steps for each subsequent serial anchor in the array to create additional tensioned and locked stitches. In some embodiments, at least four anchors are in the array, others include at least six or eight or twelve.

The step of implanting each anchor includes transtendinous insertion of the anchor through a tendon to be repaired and into a preformed bone hole having a diameter of less than about 3.0 mm. Subsequent implanted anchors can be positioned less than or equal to about 7.0 mm. from the previous implanted anchor. In practice, the tendon to be repaired has been separated from an original footprint thereof, and the anchors are implanted in a medial portion of the original footprint. The array of suture stitches formed between subsequent anchors can follow a line in the medial portion of the original tendon footprint generally perpendicular to a direction of the tendon. For example, the number of anchors in the plurality of anchors can be eight and the anchors are implanted in the original tendon footprint in a generally linear row perpendicular to the tendon direction to form seven stitches therein. The method can include implanting a second suture array laterally spaced from the first suture array.

An alternative method can include creating a serial array of tensioned and independently locked anchor to anchor suture stitches to attach soft tissue to bone. Such method includes first providing a plurality of toggle bodies, each having an elongate body portion. The first anchor in the array can include two holes, while the second and subsequent anchors (except the last anchor) each include five holes therethrough. The last anchor includes three holes. The number of holes included is based on the number of cinchable loops connecting the anchor and also the presence of a locking loop on the particular anchor as described below.

The first anchor, with two holes, has the cinchable working loop suture pass into the top of the anchor in the first hole, out the bottom, then back up through the anchor via the second hole. Both legs extend to the second anchor which has five holes (or four holes if one is a slot for receiving two suture strands). One leg passes through the top of a first hole, out the bottom and then back up though the bottom of a second hole, out the top of the second hole and forms the tensionable tail. The second leg forms the slip knot or other sliding knot structure around the tensionable tail adjacent the top of the second hole in the second anchor. The third hole has an independent locking loop extending from the third hole passage at the bottom surface with each locking loop encircling a portion of the length of the suture of the cinchable loop extending adjacent the third passage along the bottom surface, the locking loop having a first open position allowing the suture to slide through the locking loop and a second closed position engaging the suture and preventing sliding of the suture within the locking loop which maintains the tensioned size of the cinchable loop and formed stitch. The fourth and fifth passages in the second anchor function like the first and second holes in the first anchor in that another cinchable loop passes therethrough and extends to a third anchor with the structure described repeated for the array, except the last anchor which only include three holes since there is no subsequent anchor to attach in the array.

As a first step, a first toggle body of the pre-strung plurality of anchors is implanted in bone. Next, a second toggle body in the pre-strung plurality of anchors is implanted in bone spaced a selected distance from the first toggle body. Tension is then applied to the cinchable suture loop extending from the first toggle body and passing through the second toggle body. Once tensioned sufficiently by shrinking the cinchable suture loop, the loop tension is locked by locking the locking loop at the second toggle body. This creates a single tensioned and locked stitch between the first and second toggle body.

A third toggle body in the pre-strung plurality of anchors is implanted in bone spaced a selected distance from the second toggle body. Tension is applied to the cinchable working suture loop extending from the second toggle body and passing through the third toggle body. Once tensioned, the locking suture adjacent the third toggle body is locked by closing the locking loop to create a single tensioned and locked stitch between the second and third toggle body. As in other embodiments, the steps of implanting, tensioning and locking can be repeated for each subsequent serial toggle body in the array to create additional serial single suture tensioned and locked stitches. Any number of anchors can be included in the pre-strung array but it is preferred at least four are included, preferably 6, 8 or 12 in order to create a substantial array of anchor-to-anchor successive stitches.

The step of implanting each anchor can include transtendinous insertion of the anchor into a preformed bone hole having a diameter of less than about 3.0 mm. Further, each implanted anchor can be less than or equal to about 7.0 mm. from the previous implanted anchor. In practicing the methods of the present application, the tendon to be repaired has been at least partially separated from an original footprint thereof, and at least a portion of the anchors are implanted in a medial portion of the original footprint of the repaired tendon. The implanted array of stitches follows a line across at least a portion of the original tendon footprint generally perpendicular to the tendon direction. For example, the plurality of anchors can be 8 and the anchors can be implanted in the original tendon footprint in a generally linear row perpendicular to the tendon direction to form 7 stitches therein. A second array can be implanted laterally from the first suture array.

In another preferred method for attaching soft tissue to bone, a first step is to implant a first anchor of a pre-strung plurality of anchors in bone. The pre-strung plurality of anchors includes a plurality of anchors each having at least one passage therethrough, and an independent cinchable working suture loop connecting each anchor in the series to the next anchor. Each of the anchors, with the exception of the first anchor in the series, further includes a separate locking loop that encircles a portion of the length of the cinchable working suture loop adjacent the anchor of the locking loop, each locking loop having a first position allowing the working suture to slide through the locking loop and a second position engaging the working suture and preventing sliding within the locking loop. At least a first and a second anchor in the pre-strung plurality of anchors are implanted in bone spaced a selected distance with the cinchable working suture loop extending therebetween. Tension is applied to the tail of the cinchable working suture loop to tighten a portion of the working suture loop and form a suture stitch between anchors. This is followed by locking the working suture loop at the second anchor after tensioning to create a first tensioned and locked stitch between the first and second anchors.

The above steps can be repeated for at least a third serial anchor in the array to create additional serial suture tensioned and locked stitches. The step of implanting the first anchor can include forming a hole in the bone, followed by pressing the first anchor into the hole, with a central axis of the first anchor parallel to a central axis of the hole. This is followed by turning the first anchor so that the central axis of the first anchor is no longer parallel to the central axis of the hole. This can be repeated for the second anchor by forming a hole in the bone; pressing the second anchor into the hole, with a central axis of the second anchor parallel to a central axis of the hole and turning the second anchor so that the central axis of the second anchor is no longer parallel to the central axis of the hole.

This overview is intended to introduce the subject matter of the present patent application. It is not intended to provide an exclusive or exhaustive explanation. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present invention includes multiple components, devices and methods to create and use an overall system for reattaching soft tissue to bone. It is particularly useful to create a robust repair of avulsed or torn tendons, such as the supraspinatus tendon, in an arthroscopic rotator cuff repair. The implants and delivery devices make possible a more efficient and reproducible anatomical repair which should have more success (i.e., lower failure rate) than current techniques. The tendon is securely attached and held with adequate force to its original footprint with very little creep during movement of the joint. This may decrease the need for a patient's shoulder to be immobilized in a sling, increase the rate of healing reattachment of tendon to bone and allow early physical therapy to idealize postoperative shoulder range of motion and strength.

The implanted array of anchors with a continuous set of anchor-to-anchor suture stitches creates a seam-like attachment akin to a sewing machine construct. Further, the small cross-sectional size of the anchors (less than 3 mm in diameter) allows the anchors to be placed in close proximity to one another (less than about 7 mm between adjacent anchors, measuring from the edge of the bone hole). This creates a very stable anchor-to-anchor suture stitch. Combining this concept with the disclosed anchor design allows the suture stitch to be tightened and locked individually when the adjacent suture anchors are implanted. This can be repeated many times to implant a row of anchors with continuous independently tensioned and locked sutures between adjacent anchors. Also, because the anchors are in a high-density array, the tension force components on the tensioned suture are more vertically applied to the top surface of the tendon (or other connective tissue) to thereby compress the tendon firmly against the footprint of the bone without creep or slippage during joint movement which idealizes the tendon healing environment.

Figure 1A:
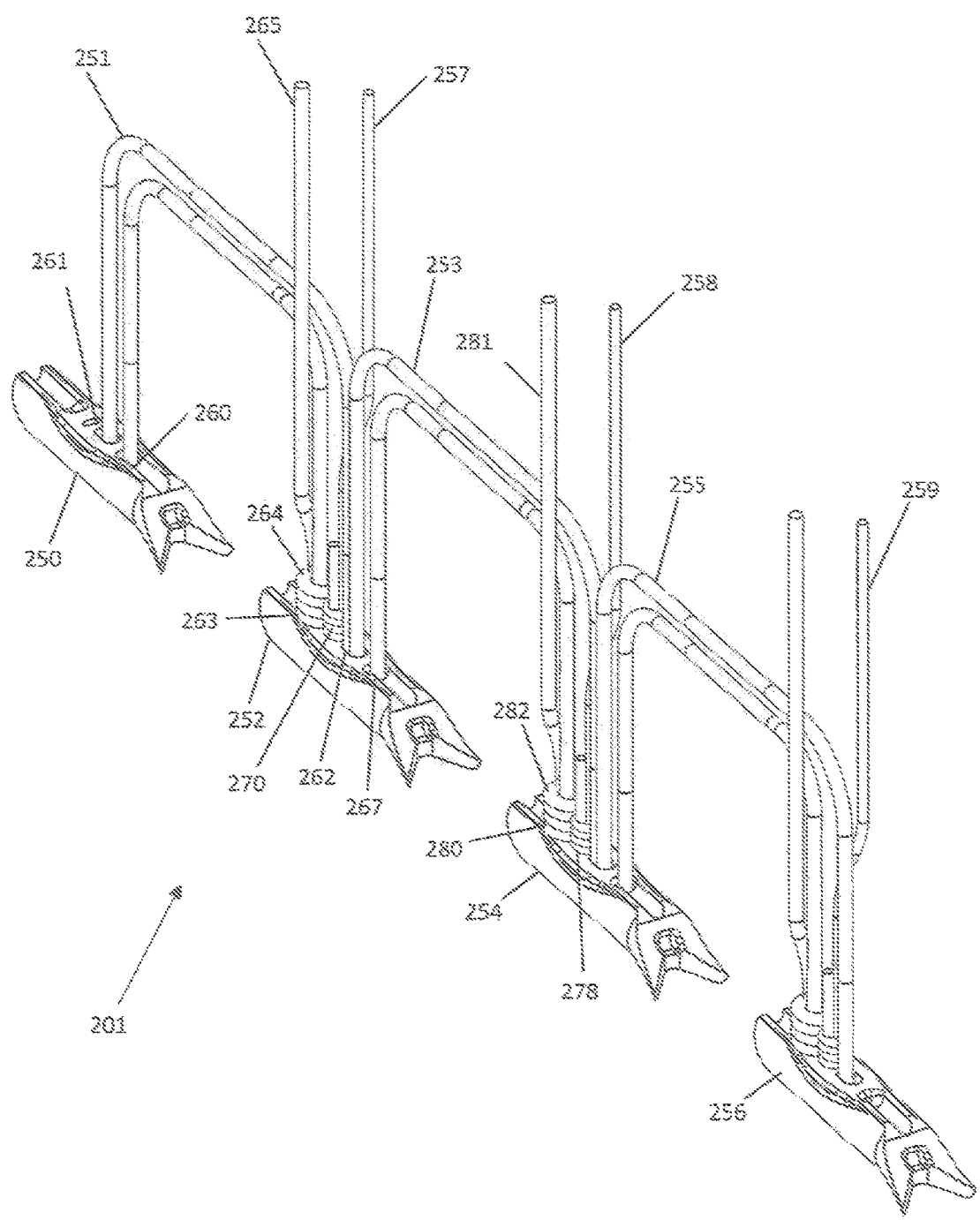
FIG. 1A is an illustration of a pre-threaded array of toggle type anchors.

In some preferred embodiments, individual anchors, as described in detail below with respect to FIGS. 2A-2F, do not function alone. Instead, each anchor is part of a pre-strung array of anchors having a plurality of cinchable independent working suture loops joining the anchors in a serial chain. FIG. 1A illustrates an exemplary pre-strung array 201. Each anchor 250, 252, 254, 256 can be implanted sequentially within the array. Upon implantation of two sequential anchors, the cinchable independent working suture loop between the two anchor 251, 253, 255 can be tensioned, then locked at the just implanted anchor so that a tensioned suture stitch formed between the two anchors provides force against the tendon to hold it in place much like a single sewn stitch. With the array, multiple continuous stitches can be formed similar to a sewn seam.

In FIG. 1A a pre-strung array 201 of individual anchors 250, 252, 254, 256 is depicted. The anchors may be similar in form and function to the anchor 100 described below. The shown array has four anchors 250, 252, 254, 256 as a representative chain. It is believed chains of 4 to 12 anchors may be useful in tendon repair procedures such as rotator cuff repair. One example includes 8 anchors in an array. As shown in FIG. 1A, the way in which each cinchable independent working suture loop 251, 253, 255 is pre-threaded through an anchor and an adjacent anchor in the series is important to assure that they will toggle as desired and tension to form the stitch when the cinchable working suture loop is tightened. The illustration shows the first anchor 250 to be implanted followed by the second anchor 252, then the third anchor 254 and finally the fourth anchor 256.

With this order of implantation understood, the first cinchable working suture loop 251 has been pre-threaded down through the top of the proximal hole 260 and back up through the distal hole 261 of the first anchor 250. The cinchable working suture loop 251 has both legs then continue to the second anchor 252 where the more distal leg is threaded down through a more proximal hole 262 and back up through a distal hole 263 of the second anchor 252. This leg of the loop continues upward to form a free leg 265 that can be tensioned to tighten the loop. The second or more proximal leg of the cinchable working suture loop extending from the first anchor extends to near the top of the distal hole 263 of the second anchor where it is used to form a slidable knot or slidable mechanism 264 in conjunction with the first leg exiting the top of the distal hole. This completes the functional cinchable working suture loop that connects the first and second anchors in the chain. Once these two anchors are implanted, pulling on the cinch loop tail 265 of the second anchor 252 collapses the loop running between the first and second anchor, takes up excess slack in the suture and forms a stitch that extends from the first anchor implant site to the second anchor implant site over the tendon surface therebetween, thus providing a first area of tendon compression against the bone beneath. The slidable knot used to collapse the loop can be a standard slip knot, a uni-knot or any other slidable structure that allows tightening the loop. For example, one leg of the suture may pass into a hollow lumen in the other leg to make a cinchable structure as is known in the art.

It is believed the above described cinchable working suture loop, when tensioned to form a stitch would have sufficient friction in the sliding knot to hold the tension placed on it and the tendon during surgery. However, unlike the area of meniscal repair, a repaired tendon in the rotator cuff, such as the supraspinatus tendon, experiences significant and numerous cyclic loading and unloading forces during use. A simple cinchable loop would likely slip open during such cyclic loads (likely greater than 180 N.) amid numerous repetitions. As such, in preferred embodiments, each implanted anchor pair having a cinchable working suture loop adjoining them in a chain also has a locking loop 270 associated with one of the anchors in the pair, preferably the second anchor of the pair in implantation order.

Figure 1B:
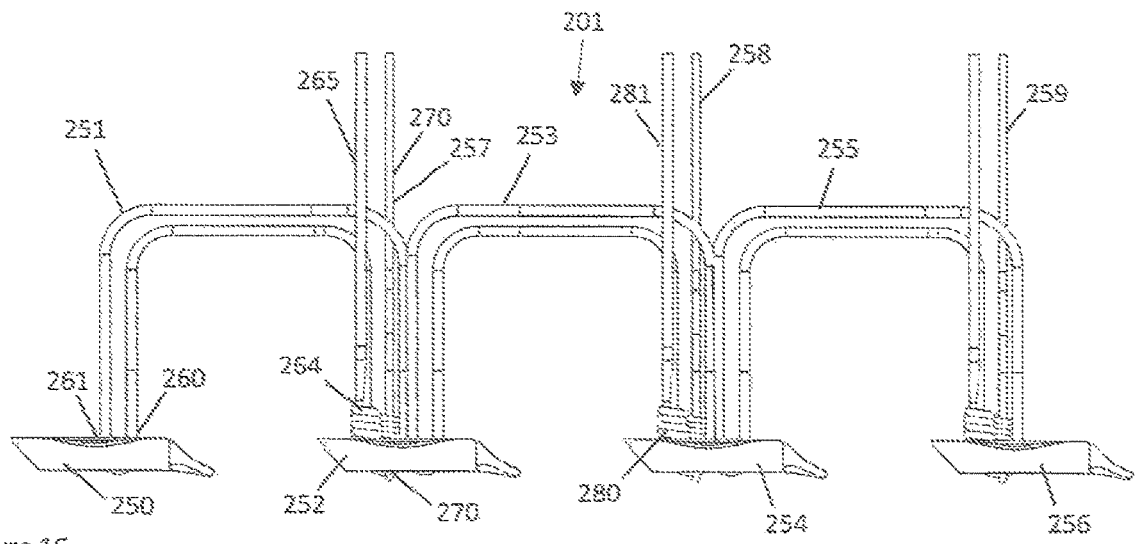
FIG. 1B is a side view of the array of FIG. 1A.
Figure 1C:
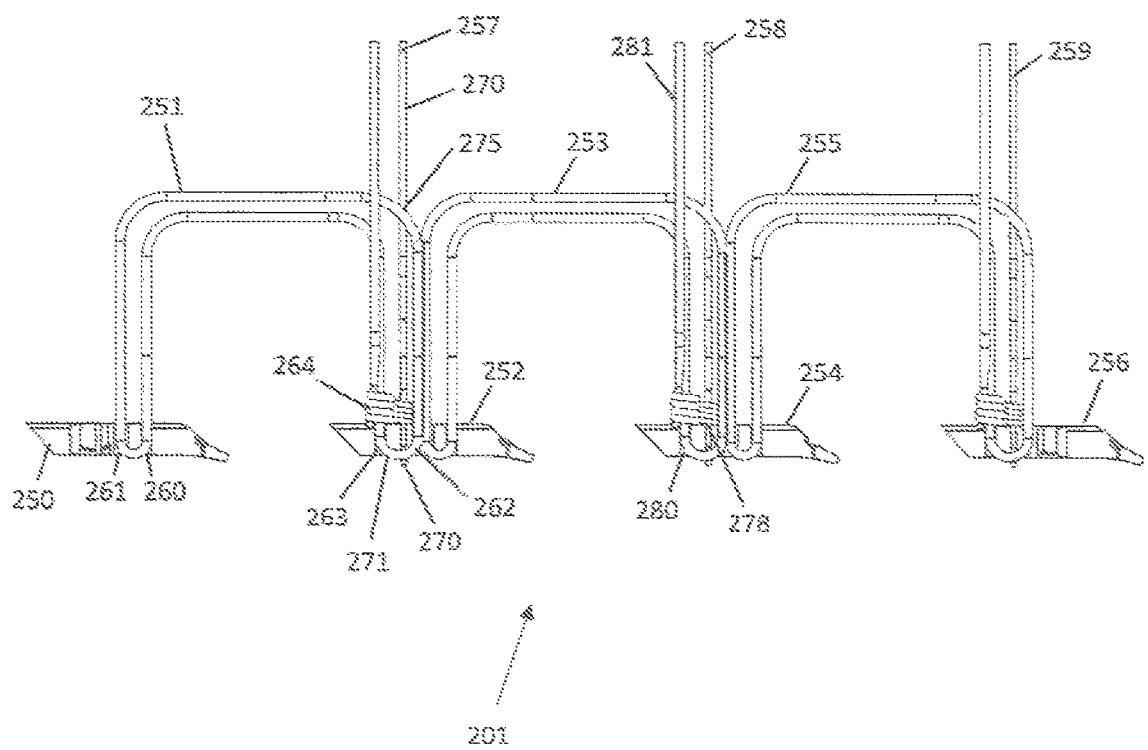
FIG. 1C is an alternative view of FIG. 1B showing the toggle anchors in cross section to illustrate the threading route of the sutures.

The locking loop 270 is indicated in FIG. 1A on the second anchor 252, however, details and function of the locking loop 270 are best understood with respect to FIGS. 1B and 1C which show a side view and a cross-sectional side view of the anchor chain, respectively. The locking loop 270 is a length of suture having a noose or collapsible loop formed on the end which is threaded into the second anchor (and other subsequent anchors) to engage the already discussed cinchable working suture loop 251. As previously discussed, both legs of the cinchable working suture loop extend from the first anchor 250 to the second anchor 252. The more distal leg 275 goes into the top of the anchor through a passage more proximal on the second anchor, comes out the bottom of the passage then extends into the bottom of the anchor at a more distal passage and up out of the top. A length of the suture 271 extends along the exterior of the bottom of the anchor between the two passages. Preferably the locking loop 270 extends through a passage in the anchor between the two passages for the legs of the cinchable working suture 251 along the anchor where a length of the suture 271 extends. The noose or loop of the locking loop 270 extends around the suture 271. In an open configuration the working suture loop can slide relative to the locking loop, however, when the locking loop is closed by tensioning the leg 257 of the loop, the cinchable working suture 251 is locked in its tensioned size and configuration so that it cannot loosen under cyclic and numerous loading and unloading.

As can be seen in the illustrations of FIGS. 1A-1C, the design of the first and the last anchor in a chain can be varied relative to the design of any number of intermediate anchors. This is because the intermediate anchor must include passages to accommodate the cinchable working suture loop of both a prior and a subsequent anchor in the chain or array of anchors. The first anchor can include one or two passages to accommodate the first cinchable working suture loop and the last anchor in any chain accommodate the last cinchable working suture in the chain plus a final locking suture loop. As illustrated for the four-anchor chain, the threading of cinchable working suture loops and the installation of locking loops is duplicated in the same way it was done for anchors one and two as is done for two and three and three and four. Of course, more intermediate anchors could be included in the array, such as a total of six, eight or even twelve or more depending upon the repair to be made in a tendon.

To be clear, a separate cinchable working suture loop 253 connects the second anchor 252 to the third anchor 254. With the order of implantation understood, the second cinchable working suture loop 253 has been pre-threaded down through the top of the proximal hole 267 and back up through the shared more distal hole 262 of the second anchor 252. The cinchable working suture loop 253 has both legs then continue to the third anchor 254 where the more distal leg is threaded down through a more proximal hole 278 and back up through a distal hole 280 of the third anchor 254. This leg of the loop continues upward to form a free leg 281 that can be tensioned to tighten the loop. The second or more proximal leg of the cinchable working suture loop extending from the second anchor extends to near the top of the distal hole 280 of the third anchor where it is used to form a slidable knot or slidable mechanism 282 in conjunction with the first leg exiting the top of the distal hole. This completes the functional cinchable working suture loop that connects the second and third anchors in the chain. Once these two anchors are implanted, pulling on the cinch loop tail 281 of the third anchor 254 collapses the loop running between the second and third anchor, takes up excess slack in the suture and forms a stitch that extends from the second anchor implant site to the third anchor implant site over the tendon surface therebetween, thus providing a second area of tendon compression against the bone beneath. The slidable knot used to collapse the loop can be a standard slip knot, a uni-knot or any other slidable structure that allows tightening the loop. For example, one leg of the suture may pass into a hollow lumen in the other leg to make a cinchable structure as is known in the art. The locking loop 258 for this second cinchable working suture loop is installed in the third anchor in the same way as the previously discussed locking loop for the first and second anchors. The above design is repeated for connecting the third anchor 254 to the fourth anchor 256 with cinchable working suture loop 255 and locking loop 259.

To create an implanted serial array of tensioned and independently locked anchor to anchor suture stitches for attaching a tendon to bone, a surgeon would begin with the pre-strung array 201 described in FIG. 1A-1C. The first anchor 250 would be implanted through the tendon into a formed bone hole. The second anchor 252 would then be implanted in close proximity to the first anchor 250, preferably less than 7 mm away. The second anchor is toggled and the cinchable working suture loop 251 is tensioned at the same time by pulling on the leg or legs that exit the distal holes 262, 263 of the second anchor 252. Tension at this location not only toggles the second anchor 252 but also tightens the cinchable working suture loop going back to the first anchor 250 to form the tensioned stitch holding the tendon against the footprint. The first cinchable working suture loop 251 is then locked so that the stitch remains tensioned and is isolated or independent of other stitches. The process is repeated for the third anchor 254 and fourth anchor 256 or more. In one preferred array, eight anchors are implanted and 7 tensioned and locked stitches in a continuous row are formed. Further, in a rotator cuff repair, multiple arrays can be implanted such as one array extending across the tendon in the medial portion of the footprint and a second array more lateral to the medial position.

FIGS. 2A-2F are a series of illustrations of exemplary toggle bodies or toggle-type anchors that can be used in a procedure for attaching tendon to bone and as members of the above-described array. The illustrations also show a more detailed cross-sectional view of the cinchable working suture loop portion threaded through the anchor along with the locking loop as threaded to interact with the cinchable working suture loop in a single anchor. The locking loop is configured to have an open position (FIG. 2E) allowing movement of the single working suture, and a closed or locked position (FIG. 2F) that prevents movement of the single working suture.

Figure 2A:
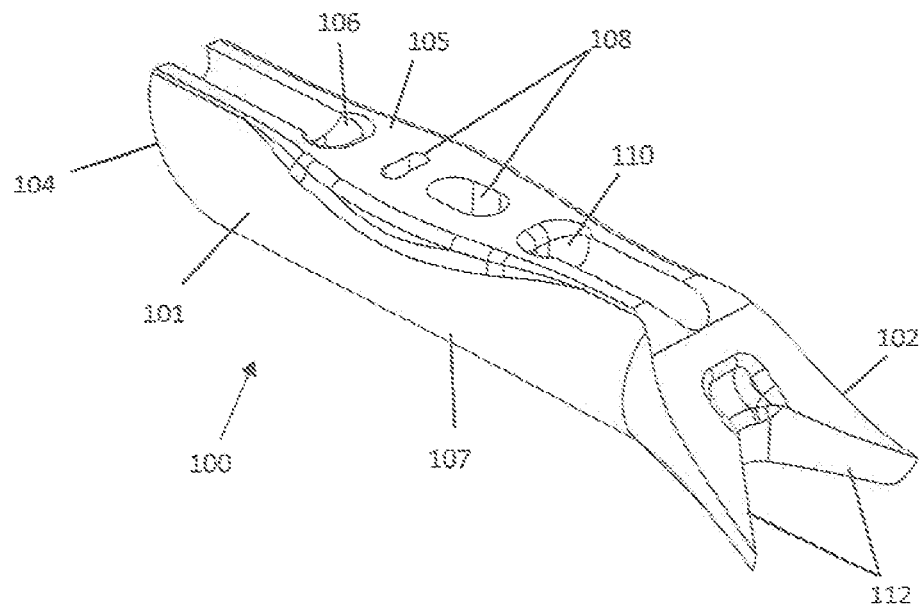
FIG. 2A is a perspective view of a representative toggle body.

Referring to FIG. 2A, a perspective view of a representative anchor in the form of an anchor body or toggle body 100 is illustrated. The toggle body 100 can be an elongate body 101 having a length defined by a proximal end 102 and a distal end 104. The elongate body 101 can be a generally cylindrical body but other shapes are possible. For example, as shown in FIG. 2A, the toggle body 100 is generally cylindrical but the top surface 105 and bottom surface 107 have flat axially-extending surfaces and/or, as shown, a semicircular depression from a proximal hole 110 to the proximal end 102 and/or from a distal hole 106 to the distal end 104, that allow room for sutures when the toggle body 100 is in a round delivery tube. The length of the toggle body 100 is substantially longer than the diameter thereof, allowing the toggle body 100 to be inserted lengthwise or axially into a small bone hole.

Once inserted, unlike most anchors used today, the entire toggle body 100 is pivoted or toggled so that it stays within the bone and has substantially its entire length compressed against material inside the bone. That is, the longitudinal axis of the toggle body 100 is rotated or pivoted from the direction used to insert through the bone hole, thereby preventing removal. This approach means that removal would require the anchor itself to fail, rather than simply being released from surrounding tissue, and provides high pullout strength (greater than 600 N before anchor failure when implanted in the array disclosed herein) from an anchor requiring a very small insertion hole (less than about 3 mm). As previously stated and described in detail below, small insertion holes allow much closer placement of anchors in a high-density array.

The toggle body 100, can have a length of about 6 mm to about 10 mm in some embodiments. This length gives adequate strength while leaving enough room inside the bone for the high number of anchors implanted. The toggle bodies are preferably molded or machined from a polymeric material, preferably a high tensile strength material such a poly-ether-ether ketone (PEEK) which is highly biocompatible. In applications where MRI imaging would not be an issue, metal can be utilized in part or all of the toggle body.

Figure 2B:
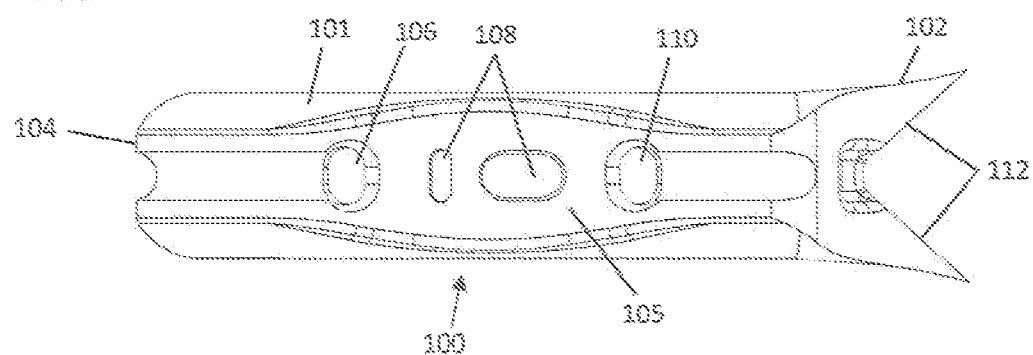
FIG. 2B is a top view of the toggle body of FIG. 2A.
Figure 2C:
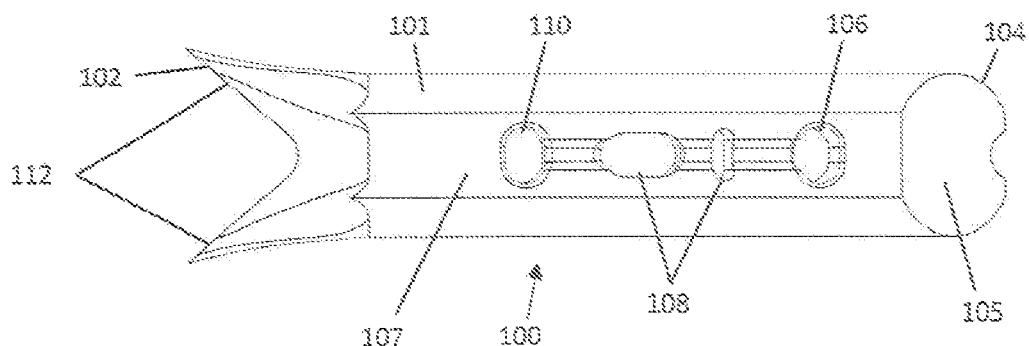
FIG. 2C is bottom view of the toggle body of FIG. 2A.
Figure 2D:
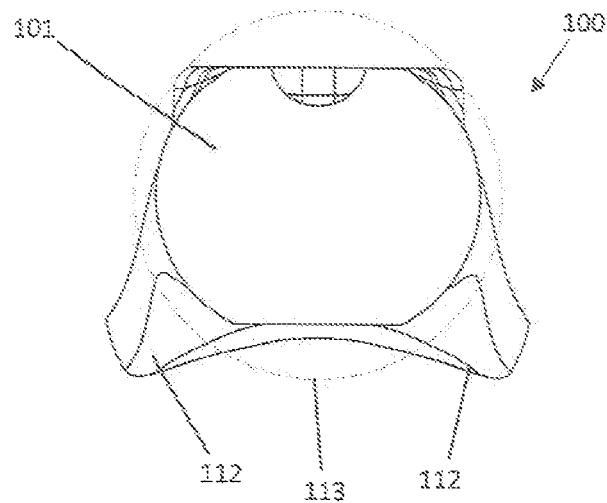
FIG. 2D is a distal end view of the toggle body of FIG. 2A.

Referring now to FIGS. 2B and 2C it can be seen that the toggle body 100 can include a number of holes or passages through the cross section thereof. As illustrated, the toggle body 100 has a proximal bore or passage 110, at least two middle passages 108, 109 and a distal passage 106. The passages 106, 108, 109, 110 extend from the top surface 105 to the bottom surface 107 such that the passages 106, 108, 109, 110 extend through the cross section of the elongate body 101. In other embodiments, the toggle body may have fewer or more bores or passages, such as having a single bore, two bores, or more than four bores. In the illustrated embodiment, the proximal passage 110 in combination with the more proximal middle passage 109 receive legs of the cinchable working suture loop that will extend to the next to be implanted anchor while the distal passage 106 in combination with the more proximal middle passage 109 receive legs of the cinchable working suture loop that comes from the prior implanted anchor in the chain. Note that in this example, the proximal middle passage is an elongated oval hole in the axial direction that allows passage of one leg from each cinchable working suture loop to pass therethrough. Separate holes could be used for each cinchable working suture loop rather than one elongated hole 109. The distal middle passage 108 receives the locking loop therethrough as described in further detail with respect to FIGS. 2E and 2F below.

The distal end 104 of the toggle body 100 has an angled surface. As shown, the angled surface creates a longer upper longitudinal surface 105 than lower longitudinal surface 107. In other words, the upper surface projects a greater distance distally than the lower surface. This is useful during insertion of the toggle body 100 because the projecting distal surface plows into cancellous spongy bone when implanted to initiate at least partial rotation of the toggle body during insertion. Keeping in mind that the present toggle bodies 100 are preferably implanted through the tendon, it is important that the toggle body 100 toggle every time or it may pull out of the bone hole under tension yet not be visible as it will be under the tendon.

The proximal end 102 of the toggle body 100 can include one or more projecting fins 112. The illustrated embodiment includes two fins 112. Each fin 112 projects outward and proximal. Further, in some embodiments, as shown, fins 112 project downward as they extend proximally. The function of the fins 112 is best understood with reference to FIG. 2D which is a distal end view of the toggle body 100. A reference circle 113 is included which indicates the general maximum cross section or diameter of the elongate body 101. The bone hole in which the implant will be placed is sized to closely match this dimension, as is the inner diameter of a delivery tube used to deliver the implant. As shown, the fins 112 project laterally beyond the maximum cross section or diameter of the elongate body. During insertion, the fins 112 flex inward under compressive force due to contact with the inner diameter of a delivery tube to fit in the bone hole. Once delivered and released from compressive forces of the delivery tube, the fins 112 relax to a size greater than the bone hole. This feature provides a safeguard against the toggle body 100 backing out of the bone hole under tension if the toggle body 100 has not adequately toggled. Further, the fins 112 are positioned so that tension on the toggle body 100 causes the partially toggled anchor to grab cancellous bone and further rotate the anchor.

Figure 2E:
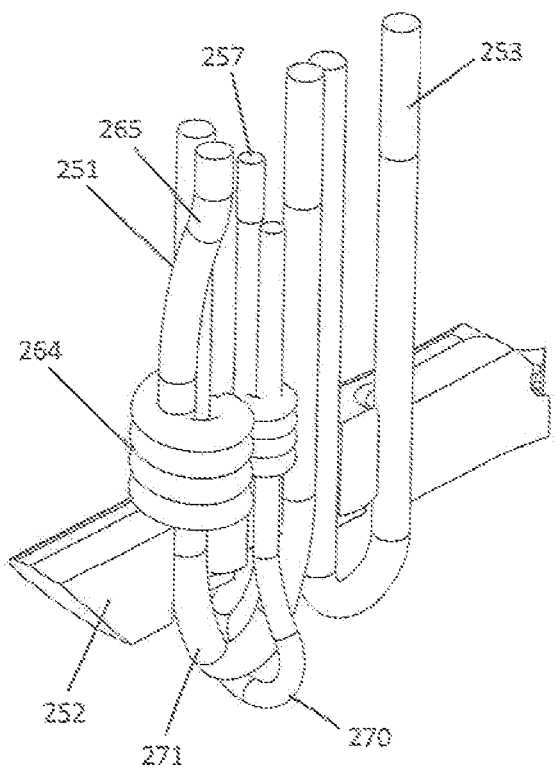
FIG. 2E is a cross-sectional view of the anchor of FIG. 2A with sutures depicted as threaded therethrough.
Figure 2F:
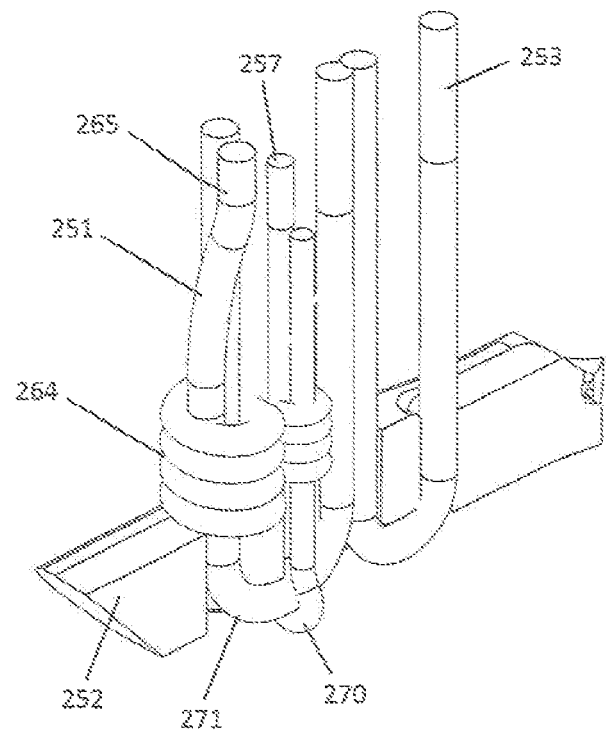
FIG. 2F is a perspective view of the anchor of FIG. 2E with the suture locking loop in a closed or locked position around the cinchable working loop suture.

In order to more fully understand the relationship between cinchable working suture loops and the locking loop in a given anchor, a partial cross section close up view of the second anchor 252 in the anchor chain is illustrated in FIGS. 2E and 2F. In FIG. 2E the locking loop 270 is in the open slidable position while in FIG. 2F the locking loop 270 has been collapsed to lock the cinchable working suture loop in size and shape as tensioned. First, the second anchor 252 includes the sliding knot portion 264 of the cinchable working suture loop extending 251 from the first anchor. It also includes a portion of the cinchable working suture loop 253 that extends to the third anchor in the chain. As illustrated, a portion 271 of the first cinchable working suture loop 251 extends adjacent the bottom of the anchor from a distal passage to a proximal middle passage. The locking suture 270 has a loop extending from a distal middle passage between the other two passage. This loop encircles the portion of the working suture extending along the bottom of the anchor. As illustrated in FIG. 2E it can be seen that the working suture can slide through the loop in this open position. Now looking to FIG. 2F, it can be seen that the locking loop 270 has been collapsed to lock the cinchable working suture loop at the size that it takes when tensioned. It cannot expand even during cyclic and numerous loading and unloading of the repaired tendon.

Several examples refer to a suture, cord, or thread, which can be used as the working suture or in the locking loop. These elements may be, for example, made of natural material such as silk and/or synthetic materials such as polyglycolic acid, polylactic acid, and polydioxanone, each of which are known for use as absorbable sutures, and/or nylon and polypropylene, which are typically non-absorbable. Various coatings, including antimicrobial, anti-wicking or lubricious coatings may be applied as well. More broadly, these elements may include any item that can be used to couple together objects in a surgical environment, such as any sufficiently biocompatible metal, natural material, plastic or other artificial material adapted for use in a surgical procedure. Monofilaments or more complex structures including braids, weaves, windings, twisted threads, coated or multilayer member, etc. may be used.

The locking loop 270 in combination with the design and location of passages through the anchor 100 is an assembly for locking a cinchable working suture loop at a fixed tensioned loop size. The locking loop 270 encircles a portion of the working suture loop, wherein collapsing the locking loop 270 compresses the cross section of the working suture adjacent the slidable knot to lock the working suture when tensioned. The suture lock 270 is preferably formed of a suture having at least a slidable knot tied therein to form the loop and to allow collapsing of the loop when a tightening leg through the distal middle passage 108 is tensioned. The distal middle passage 108 can have an upper portion for receiving the slidable knot at least partially therein that terminates in a platform within the toggle body 100 that does not allow passage of the slidable knot. Alternatively the passage can be sized small enough that the knot cannot pass through the distal middle passage includes a lower portion having an oval shape for allowing both legs of the locking loop to pass therethrough side by side and out the passage. A particularly preferred knot is a 4-throw uni knot. However, other slidable knots may be used, as desired. Further, the distal middle passage oval portion can be sized to allow movement of at least a portion of the working suture to be pulled therein in response to tension on the locking loop. The working suture is preferably a braided multistrand suture having a compressible cross-sectional area that reduces by at least about 25% when the locking loop 270 is tightened during use. The working suture may be a round No. 2 suture in some embodiments.

Figure 3A:
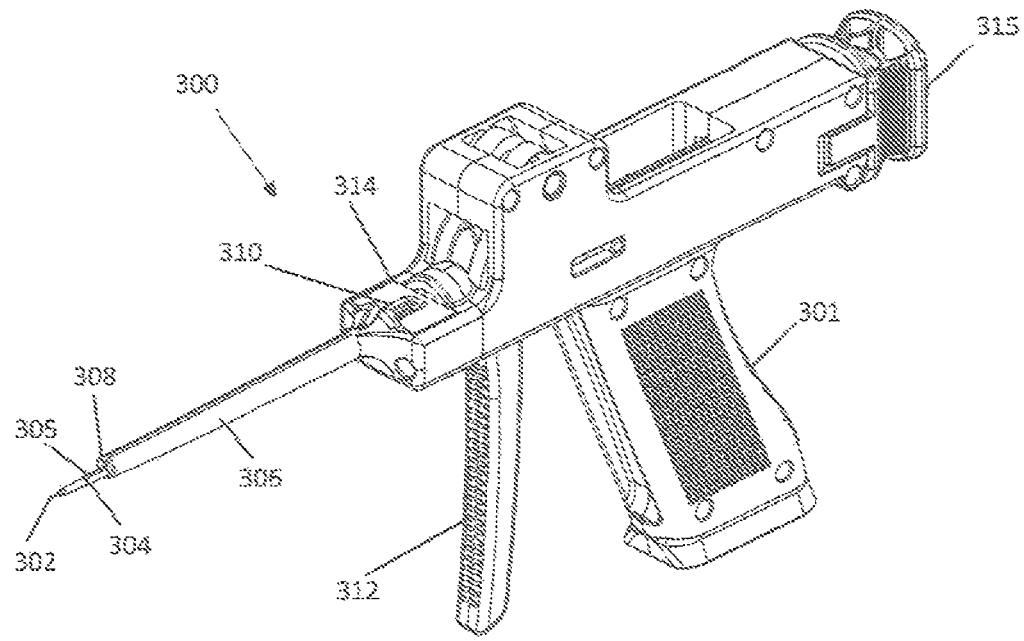
FIG. 3A is a perspective view of an example anchor delivery device.

One preferred anchor delivery device 300 for transtendinous implantation of individual anchors in an array is depicted in FIG. 3A. The delivery device 300 includes a handle assembly 301 having an outer tubular shaft 306 affixed thereto and extending distally therefrom. The outer tubular shaft 306 has a lumen extending through it. An anchor delivery tube 308 extends through the lumen of the outer tubular shaft 306 having a proximal end affixed to the handle assembly 301. The distal end of the anchor delivery tube 308 terminates distally at the same location as the outer tubular shaft 306. The distal end of the outer tubular shaft 306 along with the distal end of the anchor delivery tube 308 provide a surface that abuts the tendon when the anchor delivery device 300 is in position. It provides a bearing face that presses against the tendon and underlying bone which also counters the opposite force applied when the anchor is pulled into position. This reduces the chance of any anchor dislodging or pullout if being placed in relatively soft or fragile bone of a particular patient. Such counterforce may also avoid or prevent fracture of the bone around the bone hole during each of toggling the anchor, tensioning the working suture, and securing the suture lock.

Figure 3B:
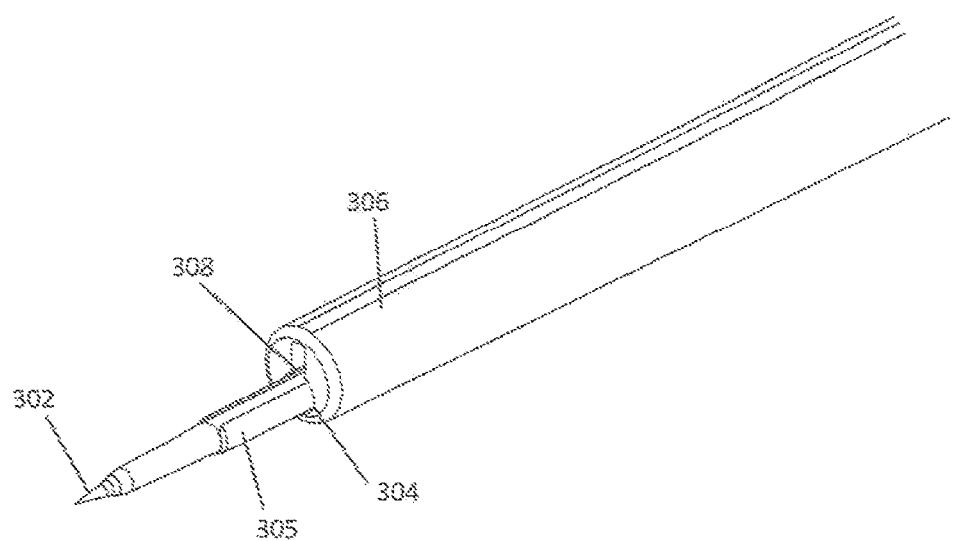
FIG. 3B is a close-up view of the distal end of the anchor delivery device of FIG. 3A showing the outer tube, delivery tube, nub and bone punch relationship.

A spring-loaded or retractable nub assembly 304 having a distal nub portion extends within the anchor delivery tube 308 and has a distal nub portion 305 extending a distance distal of the anchor delivery tube 308. The distal nub portion 305 can be retractable within the anchor delivery tube 308 when force is applied to the distal end of the nub assembly. Alternatively, the distal nub portion 305 may be retractable by application of force via a linkage and trigger or other actuator on the anchor delivery device. Further, a bone punch assembly 302 extends through the lumen of the anchor delivery tube 308 and the distal nub portion 305 with a pointed distal end terminating a distance distal of the distal end of the distal nub portion 305, wherein when fully inserted, a shoulder 314 on the bone punch assembly near the proximal end of the nub assembly blocks proximal movement or retraction of the nub portion 305, locking it in an extended position for insertion through the tendon into bone. The close-up view of the distal portion of the delivery device in FIG. 3B better shows the relationship of the outer tubular member 306, the anchor delivery tube 308, the nub assembly 304, the distal nub portion 305, and bone punch 302. As can be seen, the distal end of the bone punch 302 extends beyond the distal nub portion 305 when fully extended for use in implantation.

Figure 3C:
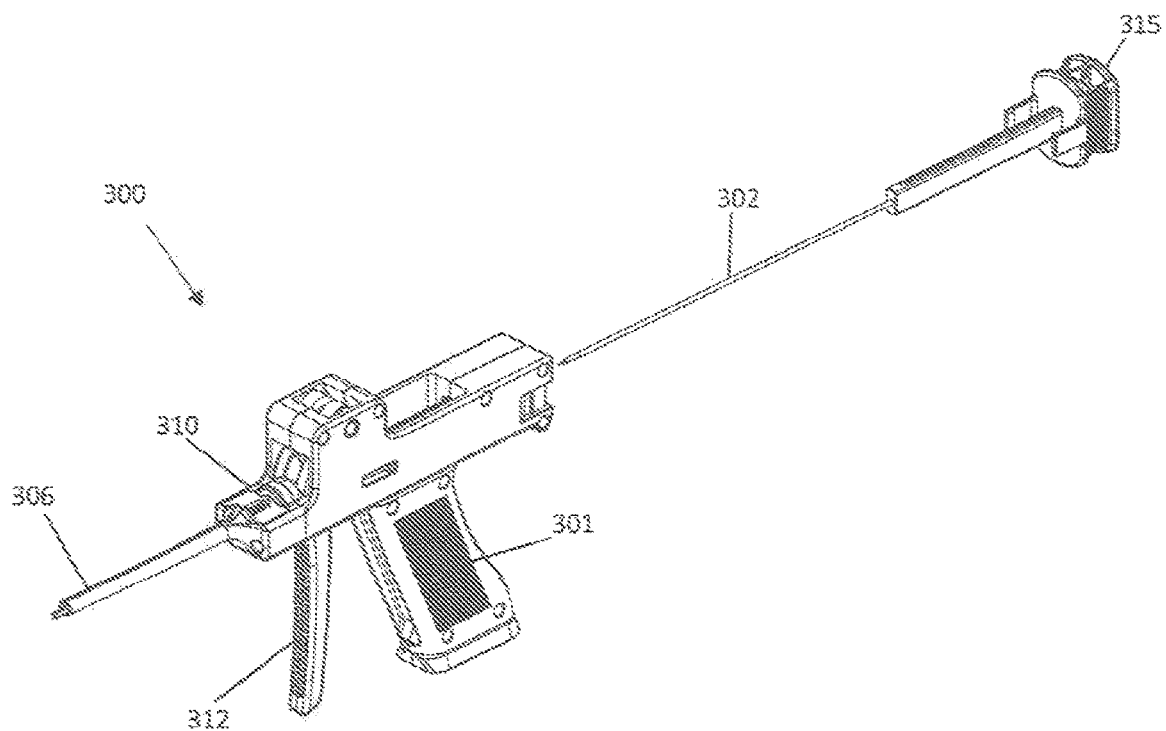
FIG. 3C is a perspective view of the delivery device of FIG. 3A with the bone punch retracted.

In some embodiments the anchor delivery tube 308 can include a longitudinal slot over its length to allow passage of sutures therethrough into the lumen of the outer tubular shaft 306. The outer tubular shaft 306 can preferably include a solid wall over its length. The delivery device also can include an anchor loading chamber 310 in communication with the proximal end of the anchor delivery tube 308 for receiving a toggle-type anchor therein. With this embodiment the bone punch assembly 302 blocks the anchor loading chamber 310 when fully inserted and allows access to the chamber 310 when retracted. A delivery device with the bone punch assembly 302 retracted is shown in FIG. 3C. The bone punch assembly 302 has a proximal end extending from the delivery device with a flat surface 315 for pounding the extended punch into bone. Additionally, a trigger lever 312 is included on the delivery device that is connected via a linkage to the bone punch. When the trigger is pulled the linkage applies a retracting force to the bone punch assembly 302 to pull the punch from bone.

Figure 3D:
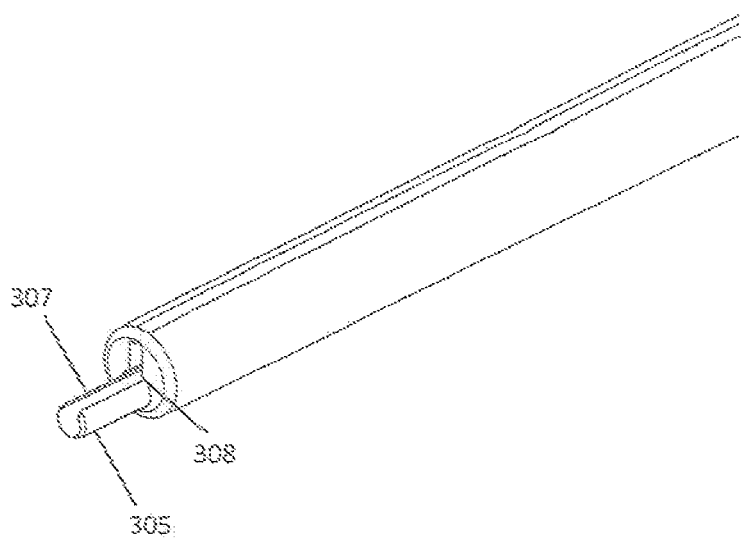
FIG. 3D is a closer view of the distal end of the delivery device of FIG. 3C showing the outer tube, delivery tube and nub relationship with the bone punch retracted.

Now referring to FIG. 3D, the distal end of the delivery device is shown with the bone punch retracted. As can be seen in the image, the distal nub portion 305 extends beyond the distal end of the anchor delivery tube 308 and outer tubular shaft 306. The distal nub portion 305 also includes a longitudinal slit 307 for passing a suture therethrough. The distal nub portion 305 can be semi-circular and may conform to the outer surface of the punch pin. It can have a thickness of about 0.0075 inches (0.19 mm) or less. With the bone punch retracted, the distal nub portion 305 is now able to move proximally into the anchor delivery tube 308 if a force is applied to the distal end of the nub assembly 304. In another example, the distal nub portion 305 may be manually retracted by the physician actuating a trigger or other structure on the anchor delivery tool. Allow retraction, or forcing retraction, may prevent the distal nub portion 305 from interfering with the toggling of an anchor and/or catching on or damaging the working suture and/or the suture lock during any of toggling, tensioning the working suture, or securing the suture lock.

Figure 3E:
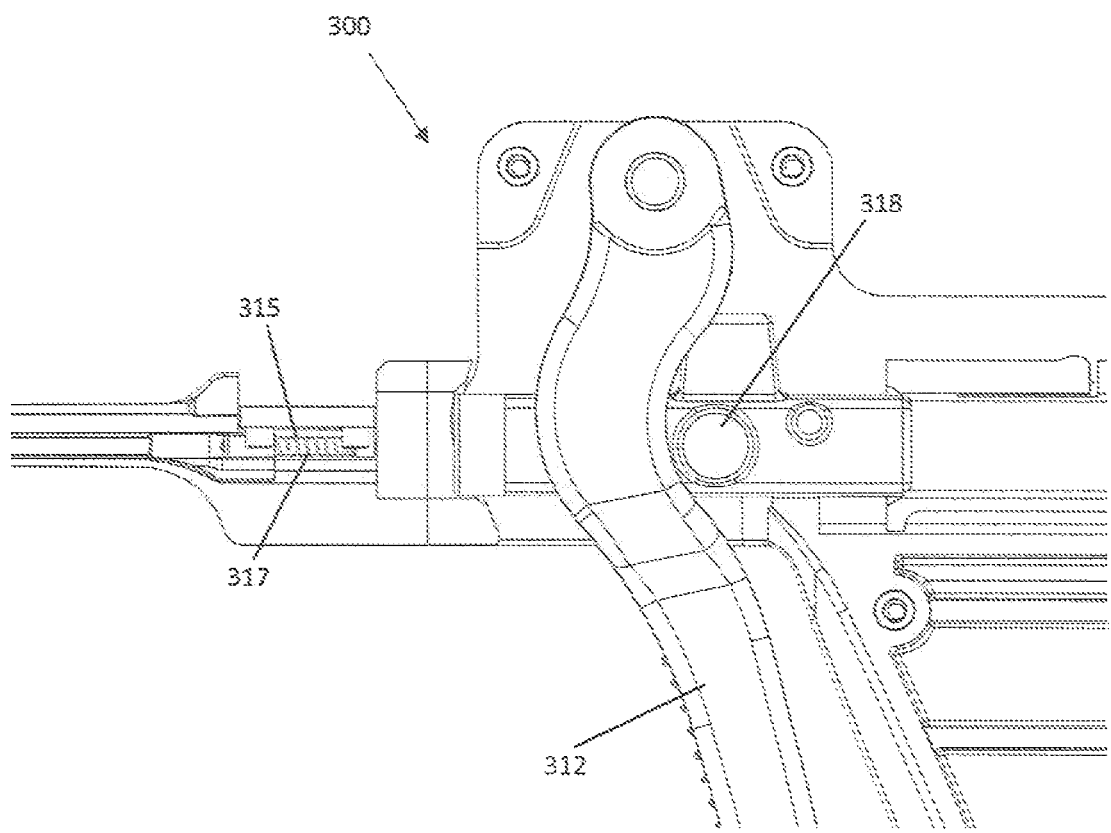
FIG. 3E is cross section view of the delivery device of FIG. 3A illustrating the mechanism to assist withdrawing the bone punch from bone and the unlocking of the nub.

More detail of the functioning of the delivery device is provided in FIG. 3E, which depicts a partial cross section view of the delivery device 300 in the portion that includes both the trigger mechanism and the proximal spring-loaded portion of the nub assembly. The pulled trigger 312 engages the punch pin boss 318 to move the entire punch pin assembly 302 proximally. When pulled proximally, the shoulder that held the proximal end of the nub assembly in a fixed position is also moved proximally. This frees the proximal end of the nub assembly 315 to move proximally against the resistive and restorative force of the spring 317. As described above, the assembly allow the distal nub portion 305 to retract into the anchor delivery tube 308 if the anchor contacts the distal nub during toggling and moving into final position.

In another example, the anchor delivery tool may be similar to that disclosed in U.S. Prov. Pat. App. No. 63/281,411, filed Nov. 19, 2021, titled DELIVERY DEVICE FOR IMPLANTING KNOTLESS MICRO-SUTURE ANCHORS AND ANCHOR ARRAYS FOR ATTACHMENT OF SOFT TISSUE TO BONE, the disclosure of which is incorporated herein by reference. The anchor delivery tool in the 63/281,411 Provisional Application is configured to use a trigger to release the punch pin from its fully extended position, while using a plunger to move an anchor from an anchor cartridge into the anchor delivery tube lumen. During the step of forming the bone hole for such an anchor delivery tool, the plunger is not depressed and no anchor is present in the anchor delivery lumen; with the plunger not depressed, the actuation of the trigger to release the punch pin is performed without releasing the nub portion 305 from a fully extended position, registered with the bone hole. During the later step of releasing the punch pin after insertion of the anchor, the plunger would be depressed (as that is how the anchor would be transferred from the cartridge to the anchor delivery lumen), and the actuation of the trigger causes retraction of both the punch pin and the nub portion 305. Other tools may be used, and the use of the toggle anchors and anchor arrays disclosed herein is not limited to these particular anchor delivery tools.

Figure 3F:
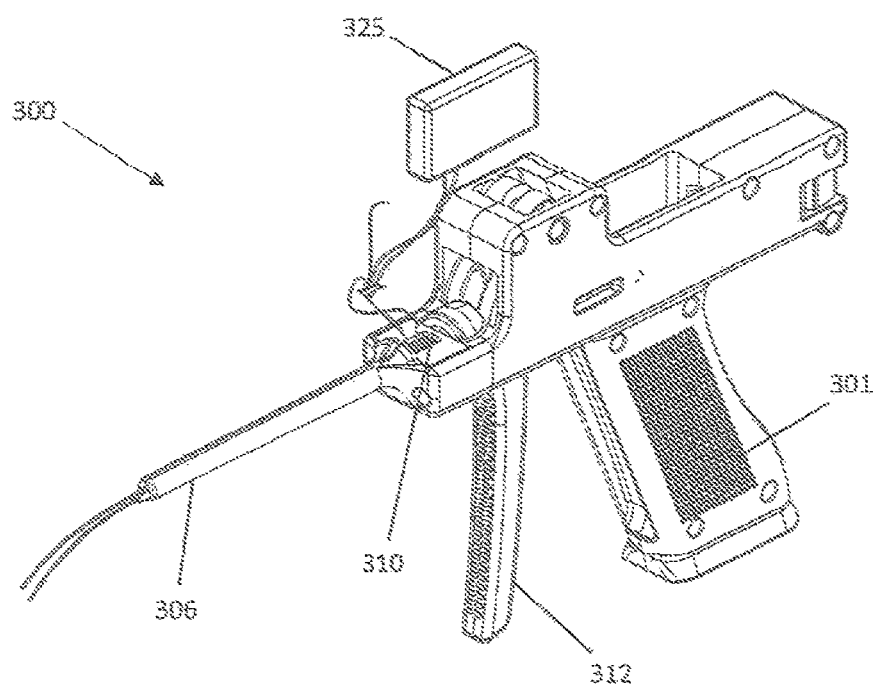
FIG. 3F is a perspective view of the delivery device of FIG. 3A and an exemplary toggle anchor cartridge.
Figure 3G:
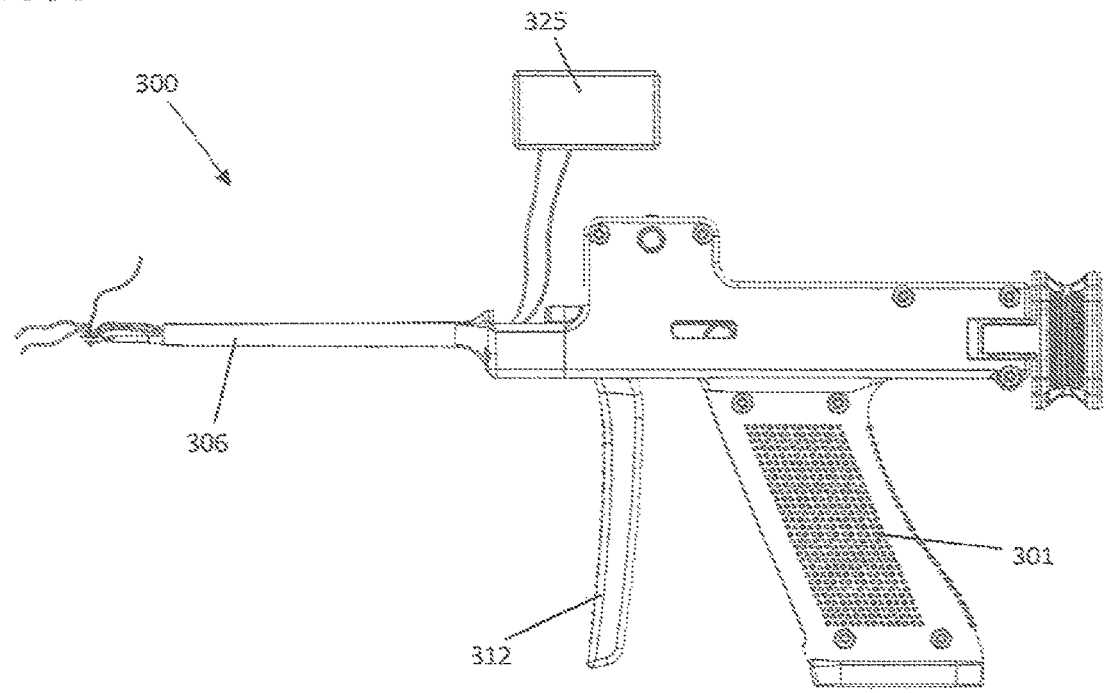
FIG. 3G illustrates a toggle anchor as it is delivered to the distal end of the delivery device.
Figure 3H:
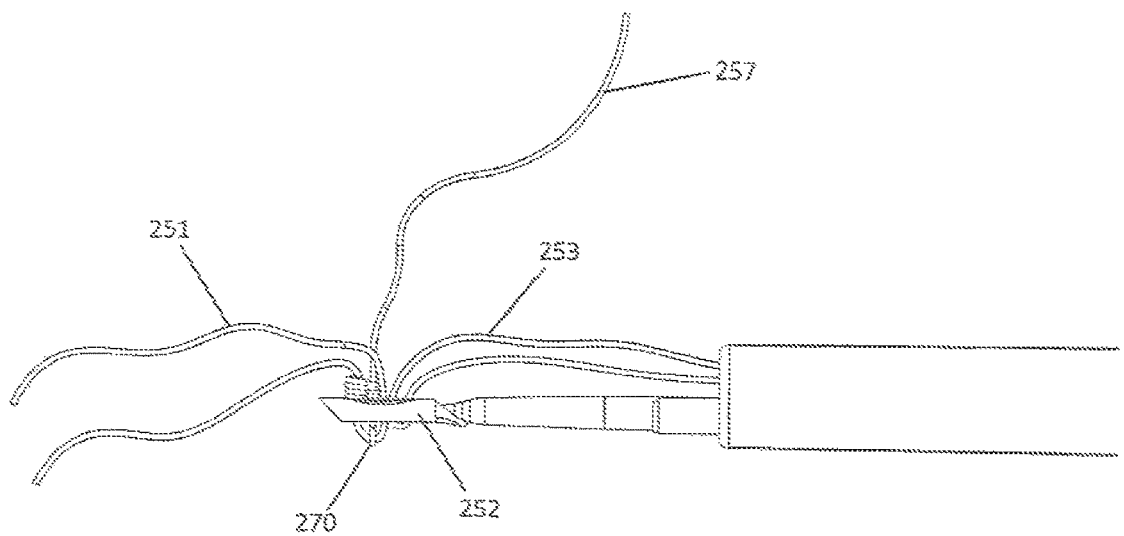
FIG. 3H is a closer view of the distal end of the delivery device and toggle anchor of FIG. 3G; and, FIGS. 4A-4I illustrate the steps for implanting exemplary anchors of the current invention and resulting pattern of continuous tensioned and locked anchor to anchor single suture stitches.

In order to use the above delivery device with an array of pre-strung toggle type anchors, certain embodiments include an anchor cartridge which is made up of individual anchor holders having suture management features. This is shown schematically in FIGS. 3F and 3G. For example, the array of FIG. 1A would have a cartridge 325 with four individual holders. Referring to FIGS. 3F, 3G and 3H, it can be seen that the cartridge is depicted with an anchor removed from the cartridge and holder. This shows the way in which the cinchable working suture loops remains threaded through both the anchor still in the cartridge and the anchor that has been removed from the cartridge. Also, a cinchable working suture loop will extend through the delivery device and out the distal end to an already implanted anchor to maintain the continuous string of anchors. FIG. 3F shows the anchor prior to loading into the delivery device. In contrast, FIG. 3G and the closer view of FIG. 3H, show the anchor as it would emerge from the distal end of the delivery device upon being pushed with the punch pin. As detailed below, the distal end would be positioned in bone of the humeral head before the anchor is implanted but shown here outside the body to understand the concept of managing the continuous chain of cinchable working suture loops and anchors in the array. For example, in FIG. 3H, if the anchor 252 is being implanted, the cinchable working suture loop 251 extends into the body to the already implanted first anchor while cinchable working suture loop 253 extends into the cartridge to the next to be implanted third anchor.

In FIGS. 4A through 4G, an exemplary method for implanting individual and an array of anchors is depicted. Further, FIGS. 4H and 4I illustrate example suture stitch arrays as implanted on the surface of a rotator cuff tendon having anchor to anchor continuous stitches that are independently tensioned and locked that can result from using this method.

Figure 4A:
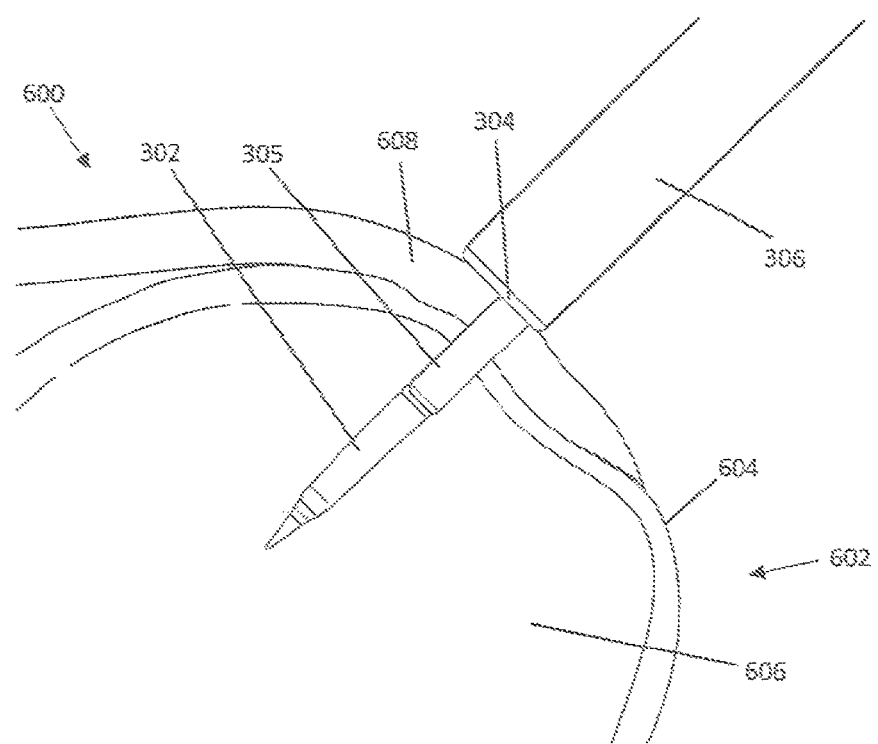

Referring first to FIG. 4A, a schematic of select parts of the shoulder rotator cuff 600 is depicted in order to explain the methods of implantation. The illustration includes a portion of the humeral head 602 including an outer cortical shell layer 604 and an inner cancellous bone material 606. A tendon 608, in this case the supraspinatus tendon 608 is shown overlaying a portion of the humeral head where it is attached to the footprint. The method is a transtendinous or through the tendon repair. The tendon 608 is first positioned in a desired location for reattachment to bone in the footprint of the original attachment. The delivery device of FIGS. 3A-3G, or similar is then utilized to implant the toggle type suture anchor through the tendon 608. To begin the delivery device is set as in FIG. 3C with the distal nub 305 extending from the distal end of the implant delivery tube 304 and outer tubular member 306. The bone punch 302 is fully inserted distally so that it extends beyond the distal end of the nub 305 and is locked in place, as is the nub locked in place. The device as configured is positioned on the tendon 608 at the desired anchor placement and pounded in until the distal end of the outer tubular member is in contact with the tendon as shown in FIG. 4A. In an alternative, the bone punch 302 and nub 305 may be in a partially extended position prior to pounding, and then become locked in their fully extended positions once the user begins tapping or pounding on the proximal end of the bone punch 302.

At this point the nub 305 extends through at least a portion of the cortical shell 604 (in thinner bone the nub 305 can extend into the cancellous bone 606) and the distal end of the bone punch 302 extends deeper into the cancellous bone 606. To achieve the desired depth of implantation to assure toggling, the bone punch extends beyond the outer tube distal end a distance of greater than or equal to about 20 mm. Further, to assure nub registration with the bone hole, the nub portion 305 extends beyond the outer tube 306 distal end a distance of about 6 to about 10 mm.

Figure 4B:
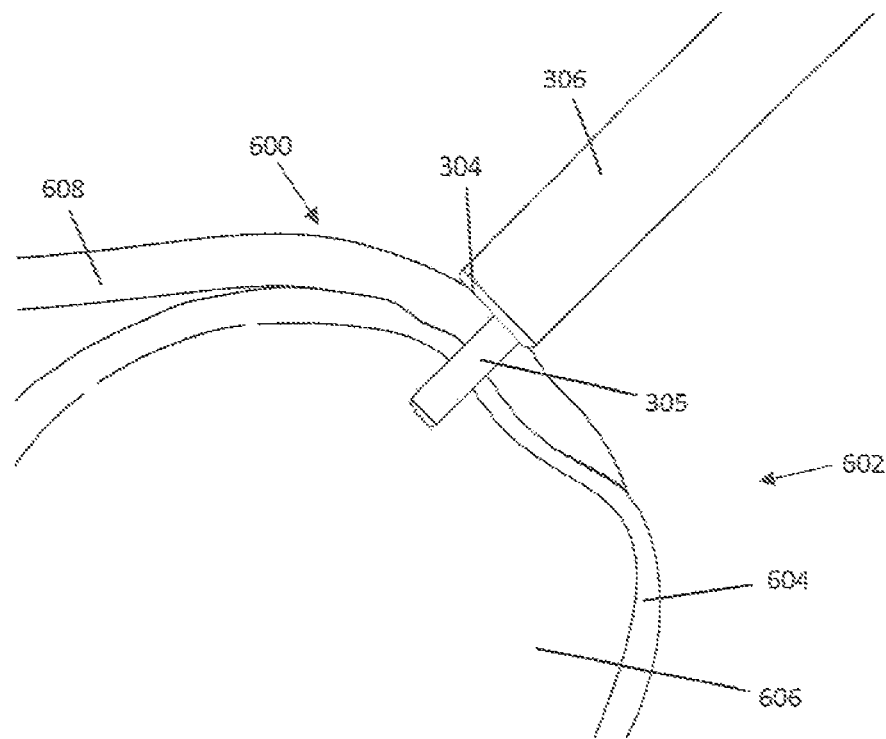

As depicted in FIG. 4B, the bone punch 302 is then retracted while maintaining the anchor delivery tube 304 and nub portion 305 in place, with the nub portion 305 providing registration with the formed hole in the bone. Absent such registration with the bone hole by the nub, the location under the tendon would be lost and it would be very difficult to feed an anchor through the tendon which would tend to fill the hole through which the bone punch traveled.

Figure 4C:
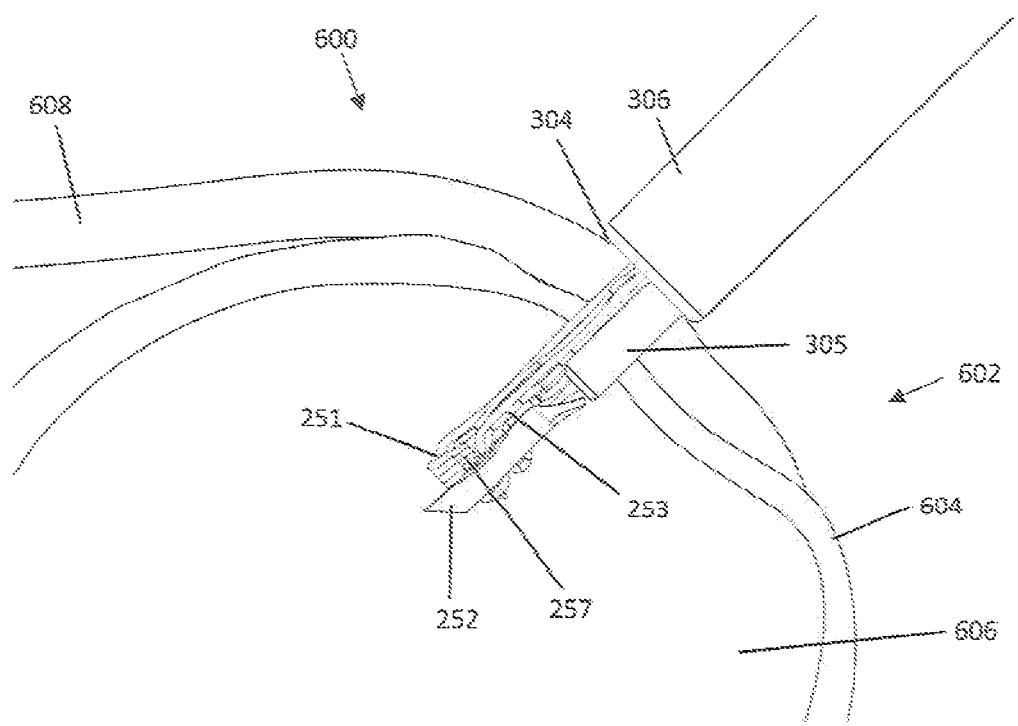
Figure 4D:
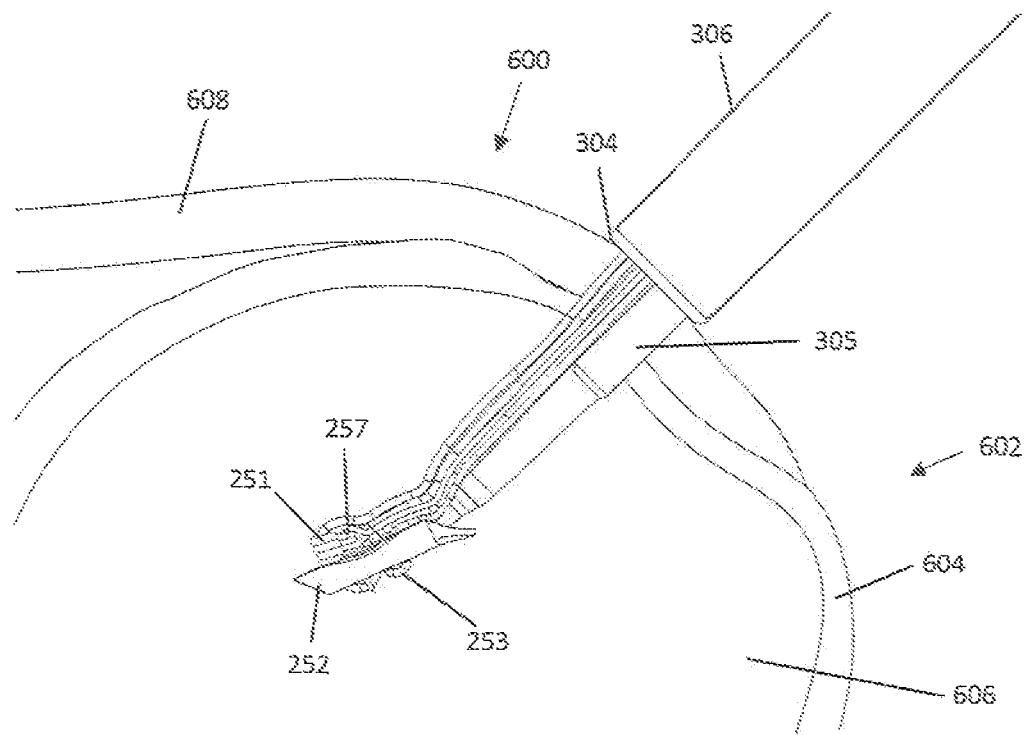

The first toggle type anchor is transferred or inserted into the proximal portion of the anchor delivery tube 306. As shown in FIG. 4C, the bone punch 302 is then reinserted into the lumen of the anchor delivery tube 304 and advanced distally. As shown in FIG. 4C, the toggle body 252 with its pre-strung cinchable working suture loops 251, 253 and locking loop 257 is pushed out the distal end by the bone punch 302. The bone punch 302 continues to be advanced in the distal direction to its original depth to push the toggle body 252 deep into the bone. It has been found that pushing the proximal end of the anchor deep into the bone with the toggle body 252 having an angled distal end causes or at least initiates rotation of the toggle body 252. The initial rotation is depicted in FIG. 4D. This initial rotation assures continued rotation upon pulling tension on the working suture loop outside the body.

Figure 4E:
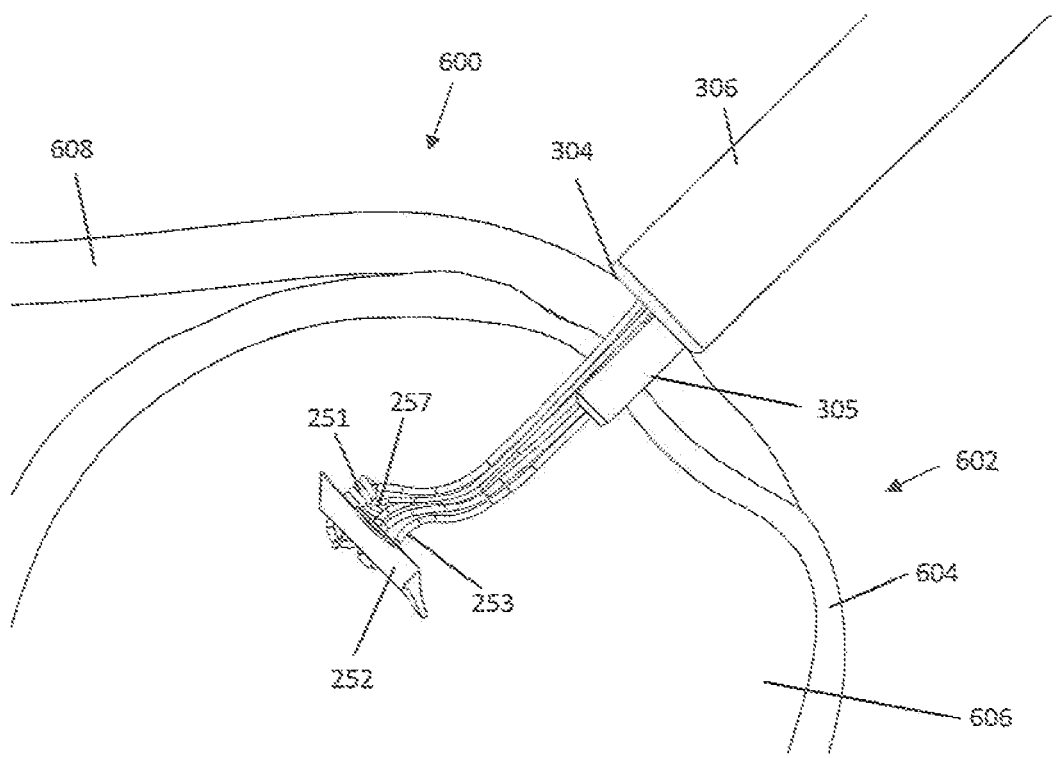
Figure 4F:
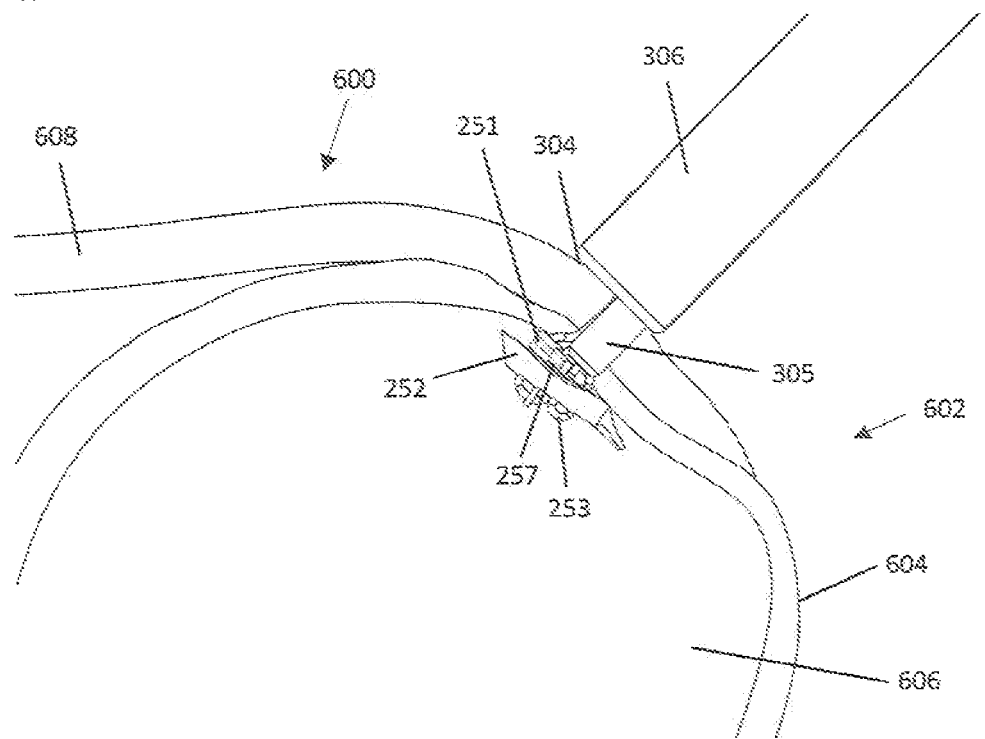
Figure 4G:
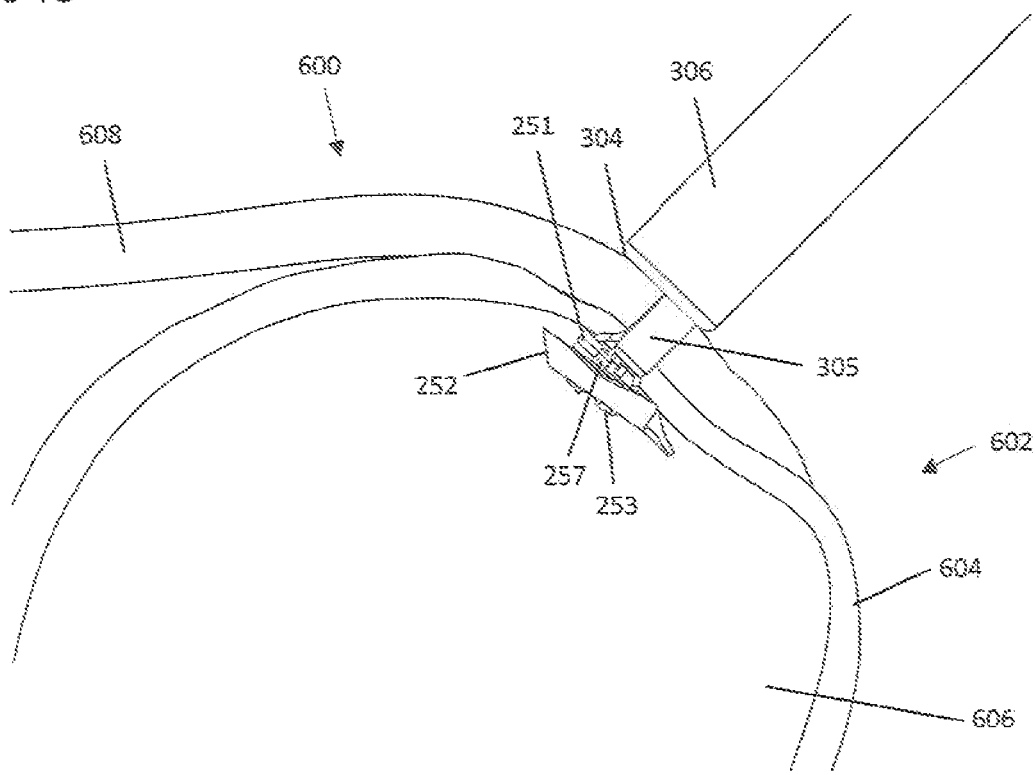
Figure 4H:
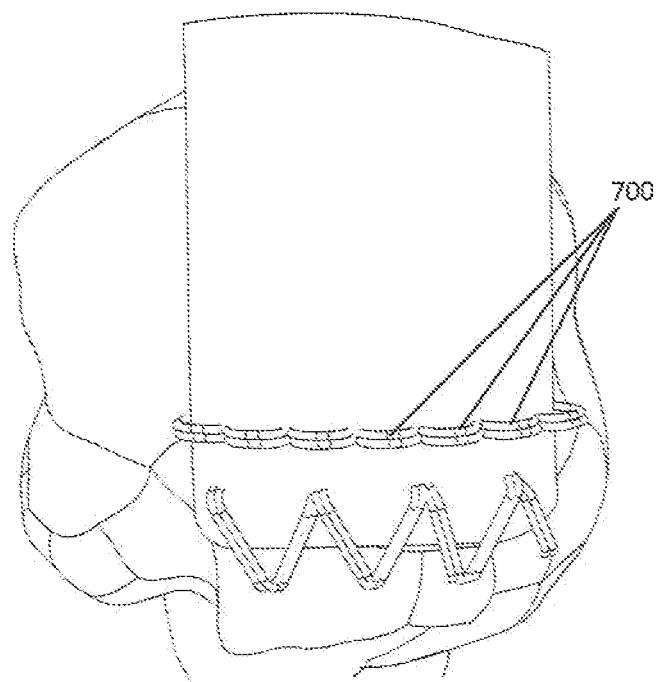
Figure 4I:
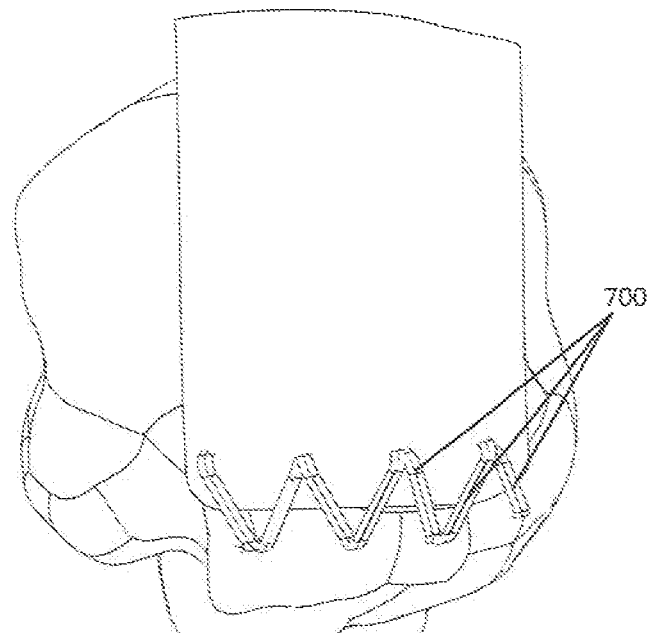

As shown in FIG. 4E, the bone punch 302 is then retracted. It is important to note that retracting the bone punch also unlocks the nub 305 so that it can retract if there is force on it from positioning the implant. This assures the nub 305 does not cut or fray the suture. The distal portion of the cinchable working suture loop extending outside the body is then pulled to complete the toggling of the anchor as aided by the proximal fins on the toggle body. This is shown in FIG. 4E. With continued tension on the working suture, the anchor 252 is pulled toward the inside surface of the cortical shell of the bone as shown in FIG. 4F. Because the nub portion 305 extends into the cancellous bone, the anchor causes it to retract proximally under spring loading so that the toggle body can reach the cortical shell if necessary. As depicted in FIG. 4G, once the cinchable working suture loop 251 is tensioned, the locking suture is tensioned to close the locking loop 270 around the cinchable working suture loop and fix the working suture relative to the anchor.

It may be observed that FIGS. 4E to 4G show the nub in an extended position as the anchor is manipulated and tensioned; in other examples, the nub may be retracted into the elongated tube 306, if desired for these steps. In addition, it should be noted that pressure may be applied against the outer surface of the tendon using the outer tubular member 306 during manipulation of the working suture and suture lock to prevent backing out of the anchor and/or to prevent cortical shell fracture.

As shown in FIGS. 4H and 4I, using the above method and device can create a row of continuous stitches 700 that closely spaced, individually tensioned and tightened. A preferred pattern includes a row of stitches generally perpendicular to the direction of the tendon as shown in FIG. 4H. Because the stitches are formed by the collapsed cinchable loop, each stitch includes two legs or strands. In a rotator cuff repair these would all be placed in a medial portion of the original tendon footprint. In some preferred embodiments a second row of anchors is also implanted, especially in a rotator cuff repair. The second row is implanted laterally of the first row and can include a zig zag pattern to put some anchors in the lateral portion of the original footprint and other lateral of the footprint to hold down edges of the torn tendon. Other configurations are also possible depending on the size and shape of the tear. For example, on a small tear a single zig zag row of stitches could be used as shown in FIG. 4I.

While the above description focuses more or less on the attachment of a tendon to bone in rotator cuff repair, the same tools, anchors and methods may be used for any re-attachment of a tendon to bone, including in other joints and locations of the body.

Additional features and alternative designs for various components, subassemblies and assemblies may be found in the following patent applications, each of which is incorporated herein by reference:

U.S. Prov. Pat. App. No. 63/172,564, filed Apr. 8, 2021, titled KNOTLESS MICRO SUTURE ANCHORS AND ANCHOR ARRAYS FOR ANATOMICAL ATTACHMENT OF SOFT TISSUE TO BONE, and U.S. patent application Ser. No. 17/551,588, filed on Dec. 15, 2021 and titled KNOTLESS MICRO SUTURE ANCHORS AND ANCHOR ARRAYS FOR ANATOMICAL ATTACHMENT OF SOFT TISSUE TO BONE.

U.S. Prov. Pat. App. No. 63/172,565, filed Apr. 8, 2021, titled TENSIONABLE AND LOCKABLE MICRO SUTURE ANCHORS AND ANCHOR ARRAYS FOR ANATOMICAL ATTACHMENT OF SOFT TISSUE TO BONE, and U.S. patent application Ser. No. 17/551,709, filed on Dec. 15, 2021 and titled TENSIONABLE AND LOCKABLE MICRO SUTURE ANCHORS AND ANCHOR ARRAYS FOR ANATOMICAL ATTACHMENT OF SOFT TISSUE TO BONE.

U.S. Prov. Pat. App. No. 63/172,614, filed Apr. 8, 2021, titled METHOD FOR CREATING A TENSIONABLE AND LOCKABLE SUTURE ANCHOR ARRAY FOR ANATOMICAL ATTACHMENT OF SOFT TISSUE TO BONE, and U.S. patent application Ser. No. 17/551,779, filed on Dec. 15, 2021 and titled METHOD FOR CREATING A TENSIONABLE AND LOCKABLE SUTURE ANCHOR ARRAY FOR ANATOMICAL ATTACHMENT OF SOFT TISSUE TO BONE.

U.S. Prov. Pat. App. No. 63/172,629, filed Apr. 8, 2021, titled DELIVERY DEVICE FOR IMPLANTING KNOTLESS MICRO-SUTURE ANCHORS AND ANCHOR ARRAYS FOR ATTACHMENT OF SOFT TISSUE TO BONE, and U.S. Prov. Pat. App. No. 63/281,411, filed Nov. 19, 2021, titled DELIVERY DEVICE FOR IMPLANTING KNOTLESS MICRO-SUTURE ANCHORS AND ANCHOR ARRAYS FOR ATTACHMENT OF SOFT TISSUE TO BONE, and U.S. patent application Ser. No. 17/551,811, filed on Dec. 15, 2021 and titled DELIVERY DEVICE FOR IMPLANTING KNOTLESS MICRO-SUTURE ANCHORS AND ANCHOR ARRAYS FOR ATTACHMENT OF SOFT TISSUE TO BONE.

U.S. Prov. Pat. App. No. 63/172,624, filed Apr. 8, 2021, titled CARTRIDGE DEVICE FOR SUTURE ANCHOR AND SUTURE MANAGEMENT DURING IMPLANTATION OF A MICRO SUTURE ANCHOR ARRAY, and U.S. patent application Ser. No. 17/551,838, filed on Dec. 15, 2021 and titled CARTRIDGE DEVICE FOR SUTURE ANCHOR AND SUTURE MANAGEMENT DURING IMPLANTATION OF A MICRO SUTURE ANCHOR ARRAY.

U.S. Prov. Pat. App. No. 63/172,568, filed Apr. 8, 2021, titled LOCKING SUTURE CONSTRUCT FOR TENSIONED SUTURE TO SUTURE BRIDGES IN ANCHOR ARRAYS FOR ATTACHING SOFT TISSUE TO BONE and U.S. patent application Ser. No. 17/551,860, filed on Dec. 15, 2021 and titled LOCKING SUTURE CON- STRUCT FOR TENSIONED SUTURE TO SUTURE STITCHES IN ANCHOR ARRAYS FOR ATTACHING SOFT TISSUE TO BONE.

U.S. Prov. Pat. App. No. 63/172,630, filed Apr. 8, 2021, titled METHODS FOR TRANSTENDINOUS IMPLANTATION OF KNOTLESS MICRO SUTURE ANCHORS AND ANCHOR ARRAYS, and U.S. patent application Ser. No. 17/551,885, filed on Dec. 15, 2021 and titled METHODS FOR TRANSTENDINOUS IMPLANTATION OF KNOTLESS MICRO SUTURE ANCHORS AND ANCHOR ARRAYS.

Each of these non-limiting examples can stand on its own or can be combined in various permutations or combinations with one or more of the other examples.

The above detailed description includes references to the accompanying drawings, which form a part of the detailed description. The drawings show, by way of illustration, specific embodiments. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, innovative subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the protection should be determined with reference to the appended claims, along with the full scope of equivalents to which such claims are entitled.

What is claimed is:

1. A pre-strung serially connected system of suture anchors for forming an implanted array with anchor to anchor tensioned and independently locked suture stitches, the system comprising:

a plurality of serially positioned toggle bodies, including a first and a last toggle body in an array having at least a first hole and a plurality of intermediate toggle bodies between the first and the last toggle bodies in the array having at least a first and a second hole through the toggle body of the plurality of intermediate toggle bodies extending from a first longitudinal surface to a second longitudinal surface of the toggle body of the plurality of intermediate toggle bodies, each hole of the at least first and second holes spaced along an elongate toggle body of the plurality of serially positioned toggle bodies;

a plurality of independent cinchable working suture loops equal in number to one less than the total number of the plurality of serially positioned toggle bodies in the array, each independent cinchable working suture loop individually connecting a previous toggle body of the plurality of serially positioned toggle bodies in the array to a subsequent toggle body of the plurality of serially positioned toggle bodies in the array, wherein each cinchable working suture loop extends through respective holes of the at least a first hole of the plurality of serially positioned toggle bodies in the previous and subsequent toggle bodies of the plurality of serially positioned toggle bodies to form a loop that can be tensioned by pulling a free tail of the loop adjacent a slip knot formed therein; and, a separate locking loop for each cinchable working suture loop, wherein the separate locking loop encircles a portion of a length of the cinchable working suture loop extending adjacent the second longitudinal surface of the toggle body of the plurality of intermediate toggle bodies, each separate locking loop having a first position allowing the cinchable working suture loop to slide through the separate locking loop and a second position engaging the cinchable working suture loop and preventing sliding within the separate locking loop to lock the cinchable working suture loop around which it encircles at each toggle body of the plurality of serially positioned toggle bodies after tensioning.

2. The system of suture anchors of claim 1, wherein at least some of the toggle bodies of the plurality of intermediate toggle bodies further comprises a third hole through the toggle body of the plurality of intermediate toggle bodies extending from the first longitudinal surface to the second longitudinal surface, wherein the separate locking loop on each anchor extends from the third hole at the second longitudinal surface after passing through the toggle body of the plurality of intermediate toggle bodies.

3. The system of suture anchors of claim 2, wherein each of the separate locking loops includes a cord having at least a slidable knot tied therein to allow collapsing of the separate locking loop when a free end of the cord extending through the third hole of each toggle body of the plurality of intermediate toggle bodies and out of the first longitudinal surface is tensioned.

4. The system of suture anchors of claim 3, wherein the third hole in each toggle body of the plurality of intermediate toggle bodies has an upper portion extending down from the first longitudinal surface for receiving the slidable knot at least partially therein from the first longitudinal surface that terminates in a platform within each of the plurality of intermediate toggle bodies that does not allow passage of the slidable knot.

5. The system of suture anchors of claim 4, wherein each separate locking loop has first and second legs, and the third hole in each toggle body of the plurality of intermediate toggle bodies includes a lower portion having an oval shape for allowing both legs of each of the separate locking loops to pass therethrough side by side and out the second longitudinal surface of each toggle body of the plurality of intermediate toggle bodies.

6. The system of suture anchors of claim 4, wherein the slidable knot is at least a 4-throw uni knot.

7. A system of toggle-type suture anchors connected serially by a plurality of independently cinchable working suture loops, the system comprising:
   a plurality of toggle bodies, each having an elongate body with a plurality of passages extending from a top surface to a bottom surface, each passage spaced along the elongate body;
   a plurality of independently cinchable working suture loops numbering one less than the plurality of toggle bodies, each cinchable working suture loop serially connecting a toggle body of the plurality of toggle bodies to the next toggle body of the plurality of toggle bodies to form a chain, wherein upon implantation the cinchable working suture loop can be tightened to form a suture stitch extending between each serial pair of toggle bodies of the plurality of toggle bodies; and,
   an independent locking loop for each cinchable working suture loop extending from a passage at the bottom surface of each toggle body of the plurality of toggle bodies, except a first toggle body of the plurality of toggle bodies in the array, each independent locking loop encircling a portion of a length of the cinchable working suture loop, each independent locking loop having a first open position allowing the cinchable working suture loop to slide through the independent locking loop and a second closed position engaging the cinchable working suture loop and preventing sliding of the cinchable working suture loop.

8. The system of toggle-type suture anchors of claim 7, wherein the elongate body of each toggle body further comprises: a pair of fins extending both proximally and radially outward from the elongate body, wherein at least a portion of each fin extends further radially beyond a maximum lateral dimension of the elongate body.

9. The system of toggle-type suture anchors of claim 7, wherein the independent locking loop of each toggle body, except for the first toggle body of the plurality of toggle bodies includes a tightening leg extending through the passage at the bottom surface and out of the passage at the top surface.

10. The system of toggle-type suture anchors of claim 9, wherein the independent locking loop of each toggle body, except for the first toggle body of the plurality of toggle bodies comprises a cord having at least a slidable knot tied therein to allow collapsing of the independent locking loop when the tightening leg through the passage at the bottom surface is tensioned.

11. The system of toggle-type suture anchors of claim 10, wherein the passage at the bottom surface of each toggle body retaining the independent locking loop has an upper portion for receiving the slidable knot at least partially therein from the top surface that terminates in a platform within the passage at the bottom surface that does not allow passage of the slidable knot.

12. The system of toggle-type suture anchors of claim 11, wherein each independent locking loop has first and second legs, wherein the passage at the bottom surface of each toggle body, except for the first toggle body of the plurality of toggle bodies retaining the independent locking loop includes a lower portion having an oval shape for allowing both legs of the independent locking loop to pass therethrough side by side and out the bottom surface.

13. The system of toggle-type suture anchors of claim 12, wherein the slidable knot is at least a 4-throw uni knot.

14. A toggle-type suture anchor system with a plurality of cinchable working suture loops joining toggle bodies in series, the system comprising:
   at least six toggle bodies, each having an elongated body having a generally flat top and bottom surfaces and rounded side surfaces, the rounded side surfaces defining a maximum diameter of the elongated body, each elongated body having at least a first and a second bore extending from the top surface to the bottom surface, each bore located at spaced intervals along the elongate body;
   at least five cinchable working suture loops, one cinchable working suture loop of the at least five cinchable working suture loops connecting each toggle body of the at least six toggle bodies to the next in a serial chain, wherein each cinchable working suture loop can be collapsed in size after toggle body implantation to form a tensioned suture stitch between each subsequent toggle body of the at least six toggle bodies; and, a locking suture for each of the at least five cinchable working suture loops, each locking suture having a collapsible loop formed therein, with the collapsible loop of each locking suture extending from a bore at the bottom surface and encircling a portion of a length of each of the at least five cinchable working suture loops extending adjacent each toggle body of the at least six toggle bodies to which it is associated, the collapsible loop of each locking suture closing in response to tension on a leg of the locking suture passing up through the bore at the bottom surface and out at the top surface.

15. The toggle-type suture anchor system of claim 14, wherein each of the locking sutures is a flexible cord having sufficient length to extend outside each toggle body of the at least six toggle bodies during use.

16. The toggle-type suture anchor system of claim 14, wherein the locking suture of each anchor comprises a cord having at least a slidable knot tied therein to allow collapsing of the collapsible loop when the tightening leg through a middle bore is tensioned.

17. The toggle-type suture anchor system of claim 14, wherein the bore at the bottom surface retaining the locking suture of each anchor has an upper portion for receiving the slidable knot at least partially therein from the top surface that terminates in a platform within the bore at the bottom surface that does not allow passage of the slidable knot.

18. The toggle-type suture anchor system of claim 17, wherein each collapsible loop has first and second legs, and wherein the bore at the bottom surface retaining each locking suture of each anchor includes a lower portion having an oval shape for allowing both legs of the collapsible loop to pass therethrough side by side and out the bottom surface.

19. The toggle-type suture anchor system of claim 18, wherein the slidable knot is at least a 4-throw uni knot.

20. The toggle-type suture anchor system of claim 18, wherein the lower portion of each anchor is sized to allow movement of at least a portion of each of the at least five cinchable working suture loops to be pulled therein in response to tension on each locking suture of the at least five cinchable working suture loops.

* * * * *